(12) United States Patent
Sakagawa et al.

(10) Patent No.: US 8,970,849 B2
(45) Date of Patent: Mar. 3, 2015

(54) TOMOGRAPHY APPARATUS AND TOMOGRAM CORRECTION PROCESSING METHOD

(75) Inventors: Yukio Sakagawa, Tokyo (JP); Makoto Sato, Tokyo (JP); Hiroyuki Yamamoto, Chigasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 540 days.

(21) Appl. No.: 13/375,259

(22) PCT Filed: Jun. 2, 2010

(86) PCT No.: PCT/JP2010/059731
§ 371 (c)(1),
(2), (4) Date: Nov. 30, 2011

(87) PCT Pub. No.: WO2011/007632
PCT Pub. Date: Jan. 20, 2011

(65) Prior Publication Data
US 2012/0075640 A1    Mar. 29, 2012

(30) Foreign Application Priority Data

Jul. 13, 2009  (JP) ................................ 2009-165053

(51) Int. Cl.
*G01B 11/02*      (2006.01)
*A61B 3/10*       (2006.01)

(52) U.S. Cl.
CPC ...................................... *A61B 3/102* (2013.01)
USPC .......................................... 356/497; 356/479

(58) Field of Classification Search
USPC ............................................... 356/479, 497
See application file for complete search history.

(56) References Cited

U.S. PATENT DOCUMENTS 6,198,540 B1 *  3/2001  Ueda et al. ..................... 356/479
6,293,674 B1 *  9/2001  Huang et al. ................... 351/221
(Continued)

FOREIGN PATENT DOCUMENTS

CN    100998493 A    7/2007
CN    101400295 A    4/2009
(Continued)

OTHER PUBLICATIONS

A.F. Fercher et al., "Measurement of Intraocular Distances by Backscattering Spectral Interferometry", Optics Communications 117, 43 (1995).
(Continued)

*Primary Examiner* — Tarifur Chowdhury
*Assistant Examiner* — Jonathon Cook
(74) *Attorney, Agent, or Firm* — Fitzpatrick, Cella, Harper & Scinto

(57) ABSTRACT

This invention realizes accurate positional offset correction between a plurality of tomograms captured by using a tomography apparatus. The invention is a tomography apparatus which corrects the positional offsets between a plurality of two-dimensional tomograms constituting a three-dimensional tomogram. This apparatus includes a tomogram analysis unit (120) which extracts feature amounts representing the tissue of a measurement target, a tomogram selection unit (140) which selects a standard two-dimensional tomogram from the plurality of two-dimensional tomograms based on the feature amounts, and a tomogram position correction unit (150) which calculates the positional offset amount between the nth two-dimensional tomogram adjacent to the standard two-dimensional tomogram and the (n−1)th two-dimensional tomogram.

8 Claims, 23 Drawing Sheets

(56) References Cited

U.S. PATENT DOCUMENTS

| | | |
|---|---|---|
| 7,417,741 B2 * | 8/2008 | Podoleanu et al. ............ 356/479 |
| 7,458,684 B2 | 12/2008 | Fukuma et al. |
| 7,480,058 B2 | 1/2009 | Zhao et al. |
| 7,744,221 B2 | 6/2010 | Wei et al. |
| 7,756,311 B2 | 7/2010 | Yasuno et al. |
| 7,864,331 B2 | 1/2011 | Termura et al. |
| 7,940,260 B2 | 5/2011 | Kriveshko |
| 8,035,637 B2 | 10/2011 | Kriveshko |
| 2006/0164653 A1 | 7/2006 | Everett et al. |
| 2006/0228011 A1 * | 10/2006 | Everett et al. ................. 382/128 |
| 2007/0159596 A1 * | 7/2007 | Fukuma et al. ............... 351/206 |
| 2007/0171220 A1 | 7/2007 | Kriveshko |
| 2007/0188765 A1 | 8/2007 | Zhao et al. |
| 2007/0195269 A1 | 8/2007 | Wei et al. |
| 2007/0236494 A1 | 10/2007 | Kriveshko |
| 2008/0117424 A1 | 5/2008 | Termura et al. |
| 2008/0312552 A1 * | 12/2008 | Zhou et al. .................... 600/558 |
| 2009/0103049 A1 | 4/2009 | McLean et al. |
| 2010/0142780 A1 * | 6/2010 | Yasuno et al. ................. 382/131 |
| 2011/0058715 A1 | 3/2011 | Doering et al. |
| 2012/0044457 A1 | 2/2012 | Sato et al. |
| 2012/0044499 A1 * | 2/2012 | Shimoyama et al. ......... 356/479 |

FOREIGN PATENT DOCUMENTS

| | | |
|---|---|---|
| CN | 101405562 A | 4/2009 |
| EP | 1775545 A2 | 4/2007 |
| JP | 2006-212153 A | 8/2006 |
| JP | 2007-130403 A | 5/2007 |
| JP | 2008-145429 A | 6/2008 |
| JP | 2008-209342 A | 9/2008 |
| JP | 2009-523547 A | 6/2009 |
| WO | 2008/012021 A1 | 1/2008 |

OTHER PUBLICATIONS

E.C.W. Lee et al., "In vivo optical frequency domain imaging of human retina and choroid", Optics Express vol. 14, No. 10 (2006).

International Search Report and Written Opinion issued in International Application No. PCT/JP2010/059731 on Jul. 20, 2010.

Nov. 20, 2013 European Search Report in European Patent Appln. No. 10799694.4.

B. Hyle Park, et al., "Real-time multi-functional optical coherence tomography," Proceedings of SPIE, vol. 4956 (2003), pp. 179-186.

Zhu Yi, et al., "A New Method to Remove Dithering in Optical Coherence Tomography without Information Loss," Laser & Infrared, vol. 37, No. 3 (Mar. 2007), pp. 288-291.

Volker Westphal, et al., "Correction of geometric and refractive image distortions in optical coherence tomography applying Fermat's principle," Optics Express 397, vol. 10, No. 9 (May 6, 2002), pp. 397-404.

Mar. 31, 2014 Chinese Official Action in Chinese Patent Appln. No. 201080031772.1.

* cited by examiner

F I G. 12
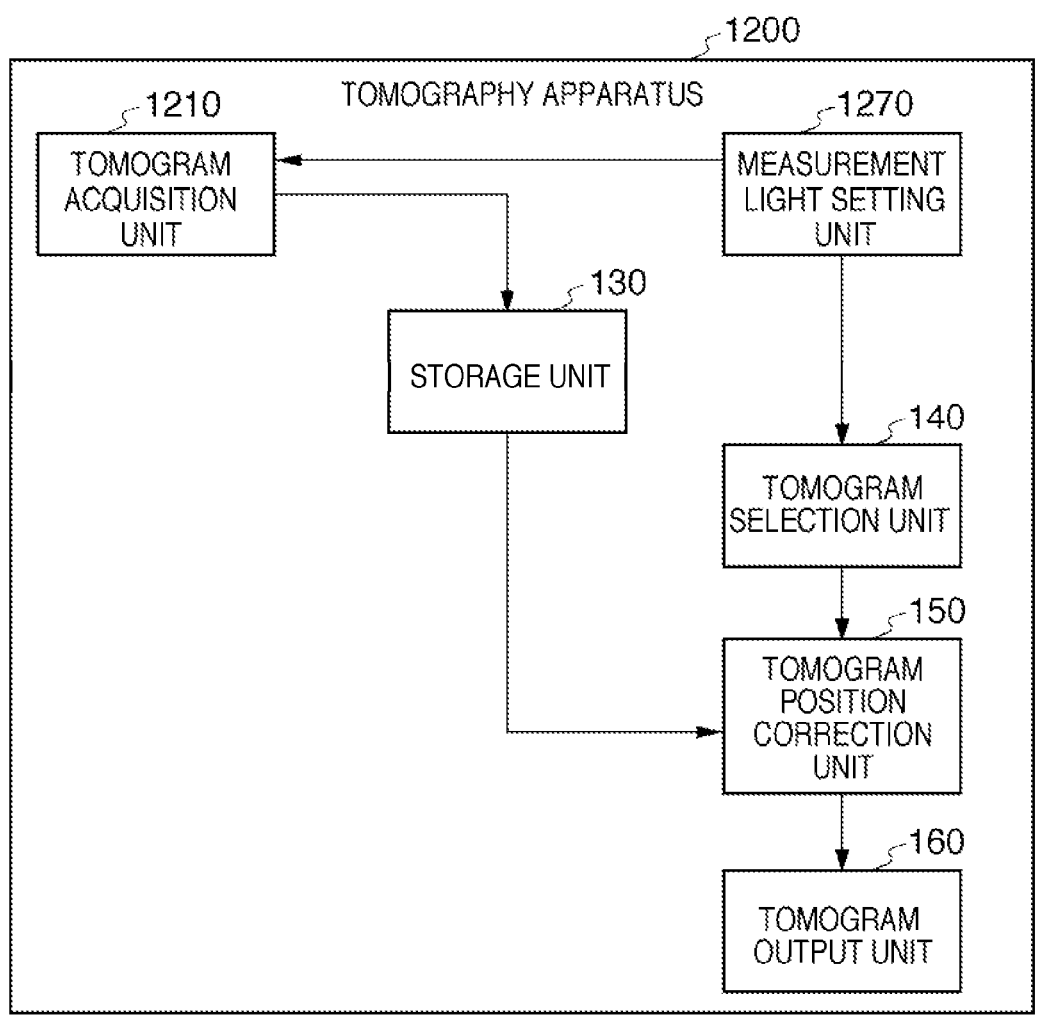

F I G. 24
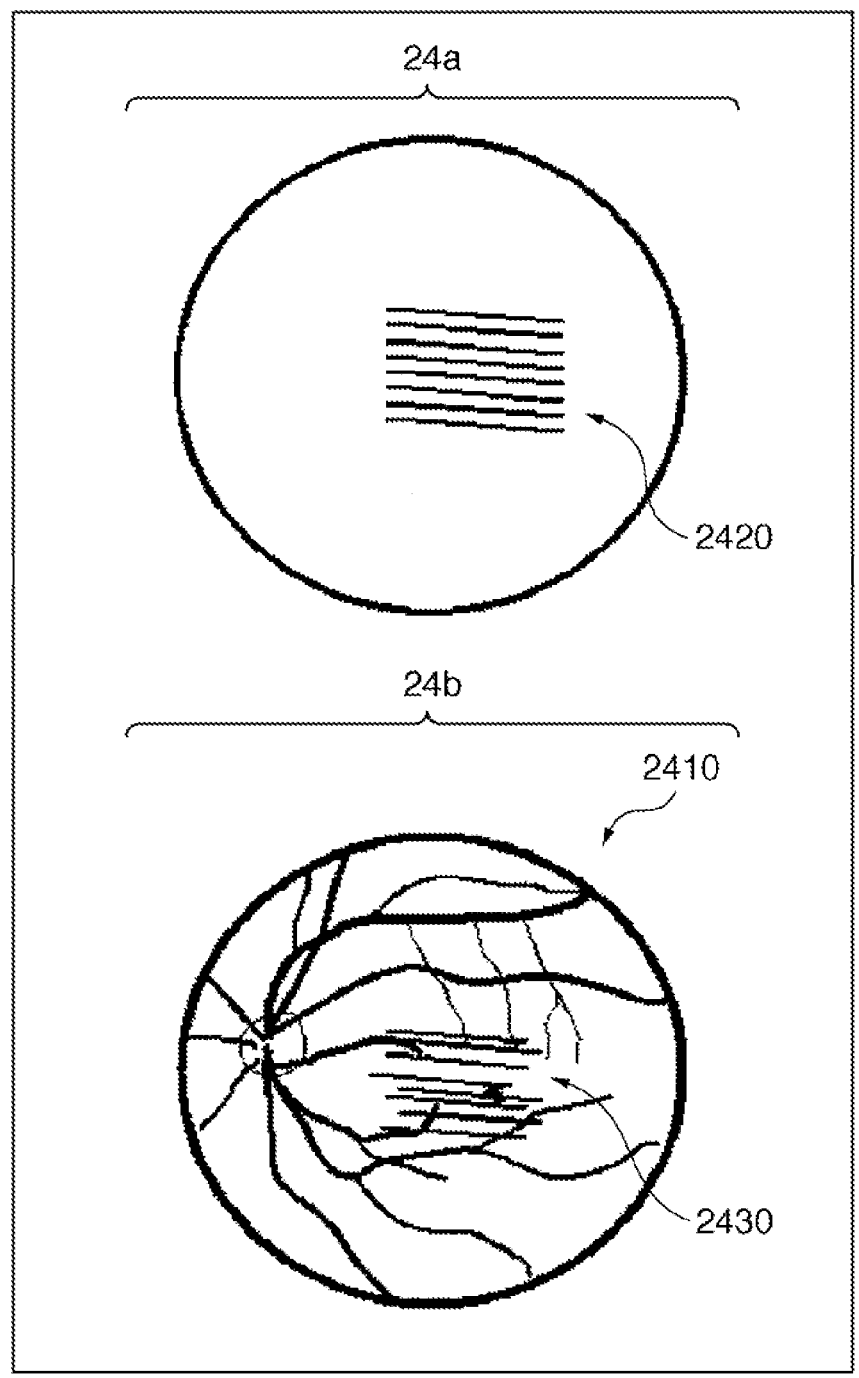

TOMOGRAPHY APPARATUS AND TOMOGRAM CORRECTION PROCESSING METHOD

TECHNICAL FIELD

The present invention relates to a tomography apparatus and a tomogram correction processing method.

BACKGROUND ART

Examination of portions of the eye has been widely practiced for the purpose of early diagnosis of life-style related diseases and various kinds of diseases ranking high in causes of blindness. In such examination on portions of the eye, it is required to find a disease in any portion of the entire eye, and hence it is required to capture an image covering a wide range of portions of the eye (a wide-area fundus image).

In general, a wide-area fundus image is captured by using a fundus camera or SLO (Scanning Laser Ophthalmoscope). Recently, the use of tomography apparatuses such as those used in optical coherence tomography has been proposed (see, for example, A. F. Fercher, C. K. Hitzenberger, G. Kamp, and S. Y. Elzaiat, "Measurement of Intraocular Distances by Backscattering Spectral Interferometry", Optics Communications 117, 43 (1995) and E. C. W. Lee, J. F. de Boer, M. Mujat, H. Lim, and S. H. Yun, "In vivo optical frequency domain imaging of human retina and choroid", Optics Express Vol. 14, No. 10 (2006). Note that optical coherence tomography will be referred to as OCT (Optical Coherence Tomography) hereinafter.

Capturing a wide-area fundus image by using a tomography apparatus such as those used in OCT allows three-dimensional observation of the state of the interior of the retinal layer. This makes it possible to quantify the state of a disease with an objective measure. Therefore, a tomography apparatus, as an apparatus for more accurate diagnosis of diseases, is increasingly expected to be used for wide-area fundus images.

Humans are involuntarily and incessantly making small eye movements (small involuntary eye movements) even when they are keeping close watch on a fixed point. For this reason, in the case of an apparatus such as those used with OCT which take a long time between the start of imaging and the end of imaging, an offset, distortion, and the like may occur between a plurality of captured tomograms due to the influence of the small involuntary eye movement of the eyes during imaging.

FIG. 24 is a view showing how an offset and distortion occur between tomograms due to the small involuntary eye movement of the eyes during imaging. Lines 2420 indicated by 24a of FIG. 24 represent imaging positions on a portion of an eye subjected to tomography. An OCT apparatus scans the highest line of the plurality of lines constituting the lines 2420 from the upper left on the drawing surface to the upper right on the drawing surface first. When the scanning position reaches the right end on the drawing surface, the OCT apparatus moves the imaging position to the next highest line, and scans it in the same manner as described above. Repeating such scanning up to the lowest line will capture a tomogram.

Lines 2430 indicated by 24b of FIG. 24 represents actual imaging positions when the OCT apparatus scans in accordance with the lines 2420 indicated by 24a of FIG. 24. As indicated by 24b of FIG. 24, the actual imaging positions are offset because of nonuniform scanning positions as well as the irregular intervals between the scanning lines due to the influence of the small involuntary eye movement of the eye portion during imaging.

To solve this problem, there has been a proposal for correcting the positional offsets between tomograms accompanying imaging position offsets by removing the influence of small involuntary eye movement during imaging. For example, Japanese Patent Laid-Open No. 2007-130403 has proposed an arrangement for correcting the positional offsets between two or more tomograms by using a reference image (one tomogram perpendicular to two or more tomograms or a fundus image).

As disclosed in patent reference 1 described above, however, in order to calculate a direction perpendicular to two or more tomograms and obtain a reference image used in the process of returning the scanning position to the origin, it is necessary to extract, in advance, feature amounts effective for calculation from the respective tomograms. In the case of a portion of an eye, the retina has a layered structure, and hence is lacking in feature amounts effective for the calculation of a direction perpendicular to each tomogram. It is therefore considered difficult to accurately correct positional offsets between tomograms by using the method disclosed in patent reference 1.

SUMMARY OF INVENTION

The present invention has been made in consideration of the above problems.

The present invention provides a tomography apparatus which corrects positional offsets between a plurality of two-dimensional tomograms constituting a three-dimensional tomogram as a measurement target, the apparatus comprising extraction means for extracting, from each of the plurality of two-dimensional tomograms, feature amounts representing a tissue of the measurement target continuously included between adjacent two-dimensional tomograms, selection means for selecting a standard two-dimensional tomogram from the plurality of two-dimensional tomograms, when the positional offsets between the plurality of two-dimensional tomograms are to be corrected, based on the feature amounts extracted by the extraction means, and calculation means for calculating the positional offset amounts of the rth two-dimensional tomogram (r is an integer equal to or more than 1) and (r−1)th two-dimensional tomogram relative to the two-dimensional tomogram selected by the selection means, based on matching between the two-dimensional tomograms.

According to the present invention, it is possible to realize accurate positional offset correction between a plurality of tomograms captured by using a tomography apparatus.

Further features of the present invention will become apparent from the following description of exemplary embodiments with reference to the attached drawings.

BRIEF DESCRIPTION OF DRAWINGS

The accompanying drawings, which are incorporated into and constitute a part of the specification, illustrate embodiments of the invention and, together with the description, serve to explain the principles of the invention.

FIG. 12 is a block diagram showing the overall arrangement of a tomography apparatus;

FIG. 24 is a view for explaining the small involuntary eye movement of a portion of an eye.

DESCRIPTION OF EMBODIMENTS

Each embodiment of the present invention will be described below with reference to the accompanying drawings. Although each embodiment to be described below will exemplify a tomography apparatus for the retinal layer (fundus retina) of a portion of an eye as a measurement target, a measurement target in the tomography apparatus according to the present invention is not limited to a fundus retina.

First Embodiment

1. Arrangement of Tomography Apparatus

Figure 1:
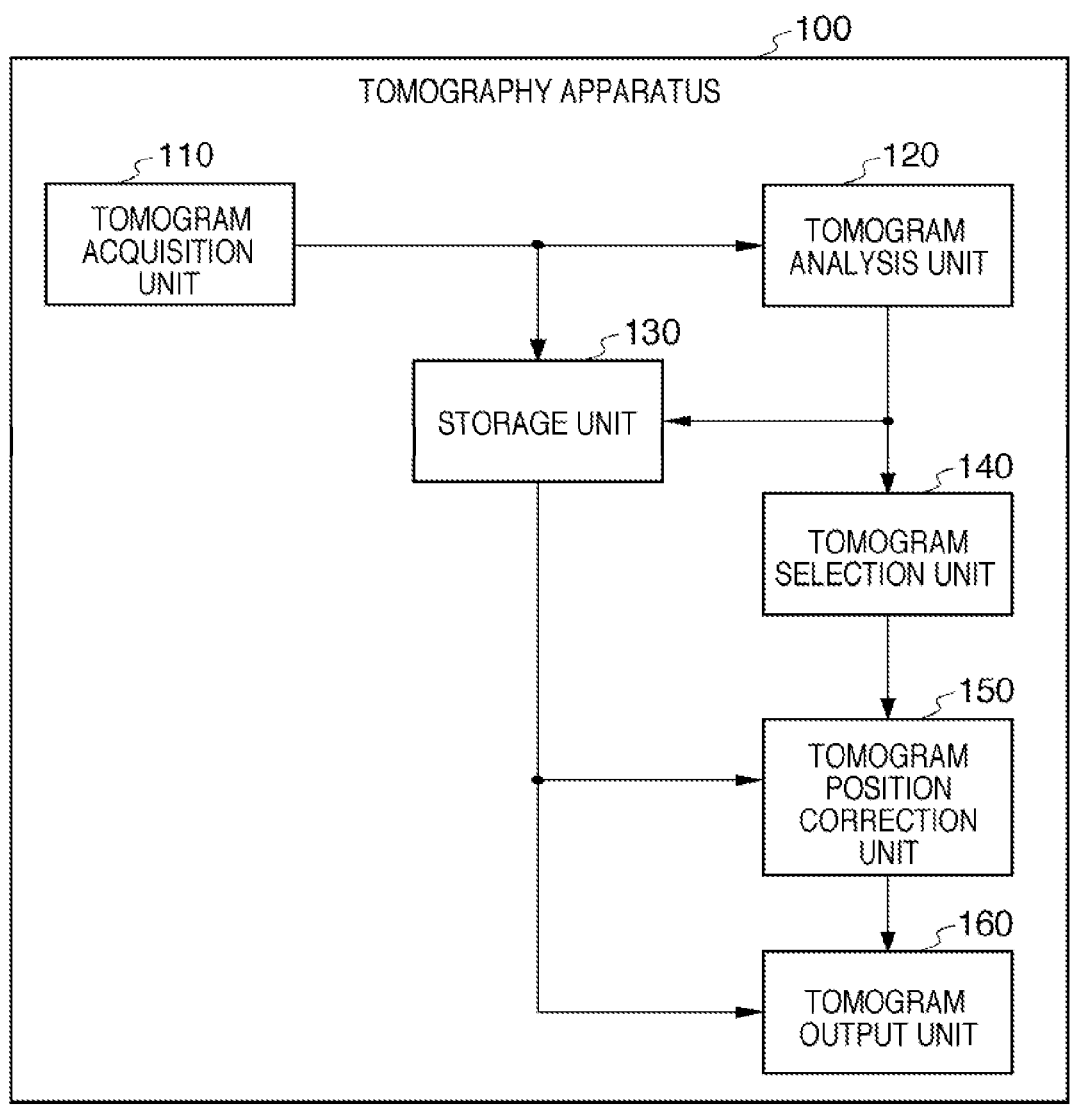
FIG. 1 is a block diagram showing the overall arrangement of a tomography apparatus.

FIG. 1 is a block diagram showing the overall arrangement of a tomography apparatus 100 according to the first embodiment of the present invention. As shown in FIG. 1, the tomography apparatus 100 includes a tomogram acquisition unit 110, a tomogram analysis unit 120, a storage unit 130, a tomogram selection unit 140, a tomogram position correction unit 150, and a tomogram output unit 160.

The tomogram acquisition unit 110 performs imaging processing of a three-dimensional tomogram of a fundus retina as a measurement target. More specifically, the tomogram acquisition unit 110 irradiates the fundus retina with measurement light, and reconstructs a three-dimensional tomogram of the fundus retina by using the interference light obtained by causing interference between reflected light from the fundus retina and reference light. The tomogram acquisition unit 110 will be described in detail later.

The units ranging from the tomogram analysis unit 120 to the tomogram position correction unit 150 store a three-dimensional tomogram captured by the tomogram acquisition unit 110, and also perform processing (tomogram position correction processing) for correcting the positional offsets between two-dimensional tomograms forming a three-dimensional tomogram having small involuntary eye movement. Tomogram position correction processing by the units ranging from the tomogram analysis unit 120 to the tomogram position correction unit 150 will be described in detail later.

The tomogram output unit 160 displays the three-dimensional tomogram captured by the tomogram acquisition unit 110 and the three-dimensional tomogram having undergone tomogram position correction processing by the units ranging from the tomogram analysis unit 120 to the tomogram position correction unit 150 on a monitor or outputs them to the outside via a network or the like.

2. Arrangement of Tomogram Acquisition Unit

Figure 2:
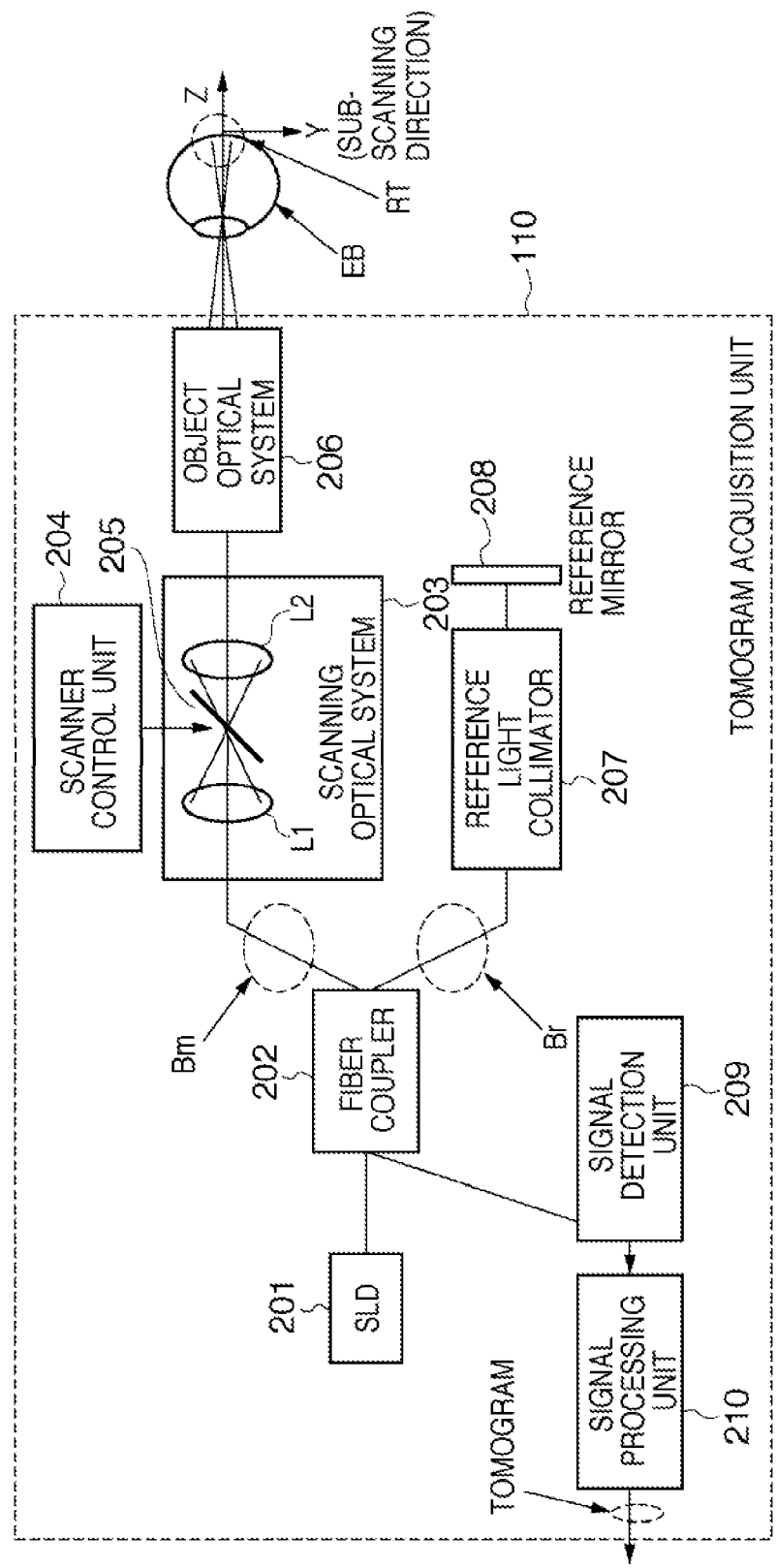
FIG. 2 is a block diagram showing the detailed arrangement of a tomogram acquisition unit.

The arrangement of the tomogram acquisition unit 110 will be described next. FIG. 2 is a block diagram showing the detailed arrangement of the tomogram acquisition unit 110.

As shown in FIG. 2, the tomogram acquisition unit 110 captures a three-dimensional tomogram of a retinal layer (fundus retina) RT of a portion of an eye EB by applying measurement light onto the fundus retina RT. The tomogram acquisition unit 110 in this embodiment uses the spectral domain system which reconstructs a three-dimensional tomogram by performing Fourier transformation of the signal detected by spectroscopy of interference light.

Note that in the following description, a direction perpendicular to the drawing surface of FIG. 2 will be referred to as an X-axis direction, and scanning of measurement light in the X-axis direction will be referred to as main scanning. In addition, scanning of measurement light in the Y-axis direction in FIG. 2 will be referred to as sub-scanning. The horizontal direction on the drawing surface of FIG. 2 (the depth direction of a portion of an eye, that is, the irradiation direction of measurement light) is defined as a Z-axis direction.

Light emitted by an SLD 201 which is a low-coherence light source strikes a fiber coupler 202. The fiber coupler 202 then separates the light into measurement light Bm and reference light Br. The measurement light Bm strikes a scanning optical system 203 through an optical fiber. The reference light Br strikes a reference light collimator 207 through an optical fiber.

The scanning optical system 203 includes a lens L1, and focuses the incident measurement light Bm on a galvanometer mirror 205. The galvanometer mirror 205 scans the fundus retina RT as a measurement target with the focused measurement light Bm.

Note that the galvanometer mirror 205 has two drive shafts. A scanner control unit 204 controls the galvanometer mirror 205 through the drive shafts so as to scan the measurement light Bm on the fundus retina RT in the main scanning direction and the sub-scanning direction.

The measurement light Bm output from the galvanometer mirror 205 reaches the fundus retina RT as a measurement target through a lens L2 and an object optical system 206. The light is then reflected by the fundus retina RT and reaches the fiber coupler 202 through the object optical system 206 and the scanning optical system 203.

On the other hand, the reference light Br emerging from the fiber coupler 202 is guided to a reference mirror 208 through the optical fiber and the reference light collimator 207. The light is reflected by the reference mirror 208 and reaches the fiber coupler 202 again to cause interference with the measurement light Bm reflected by the fundus retina RT, thereby generating interference light. The generated interference light is input to a signal detection unit 209.

The signal detection unit 209 detects the interference light and converts it into an electrical signal. The signal detection unit 209 then outputs the signal as an interference signal to a signal processing unit 210. The signal processing unit 210 generates a one-dimensional signal (to be referred to as an A-scan signal hereinafter) corresponding to the reflectance at each portion of the fundus retina RT in the Z-axis direction by performing signal processing such as Fourier transform for the interference signal, thereby reconstructing a three-dimensional tomogram of the fundus retina RT. The three-dimensional tomogram of the fundus retina RT is transmitted to the tomogram analysis unit 120 and the storage unit 130.

3. Explanation of Tomography/Correction Processing

Figure 3:
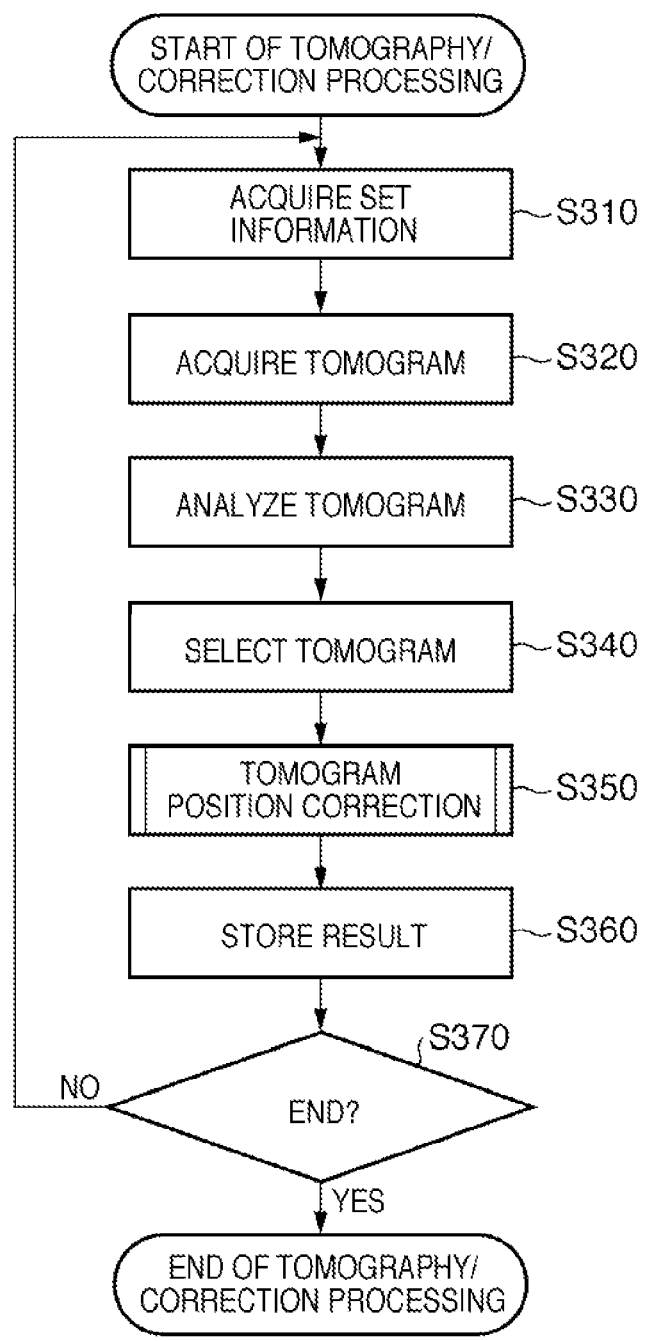
FIG. 3 is a flowchart showing a procedure for tomography/correction processing.

A procedure for tomography/correction processing in the tomography apparatus 100 will be described next. FIG. 3 is a flowchart showing a procedure for tomography/correction processing in the tomography apparatus 100.

As shown in FIG. 3, when starting tomography/correction processing, the apparatus acquires various kinds of set information input by the operator via a keyboard, a mouse, and the like (not shown) in step S310. More specifically, the apparatus acquires set information such as a region and position (measurement position) on the fundus retina RT as a measurement target, instructions concerning a scanning speed and scanning direction, the number of B-scan images (to be described in detail later) in an imaging range, and the number of A-scan signals constituting a B-scan image. The acquired set information is transmitted to the tomogram acquisition unit 110.

In step S320, the tomogram acquisition unit 110 starts capturing a three-dimensional tomogram based on the transmitted set information.

Figure 4:
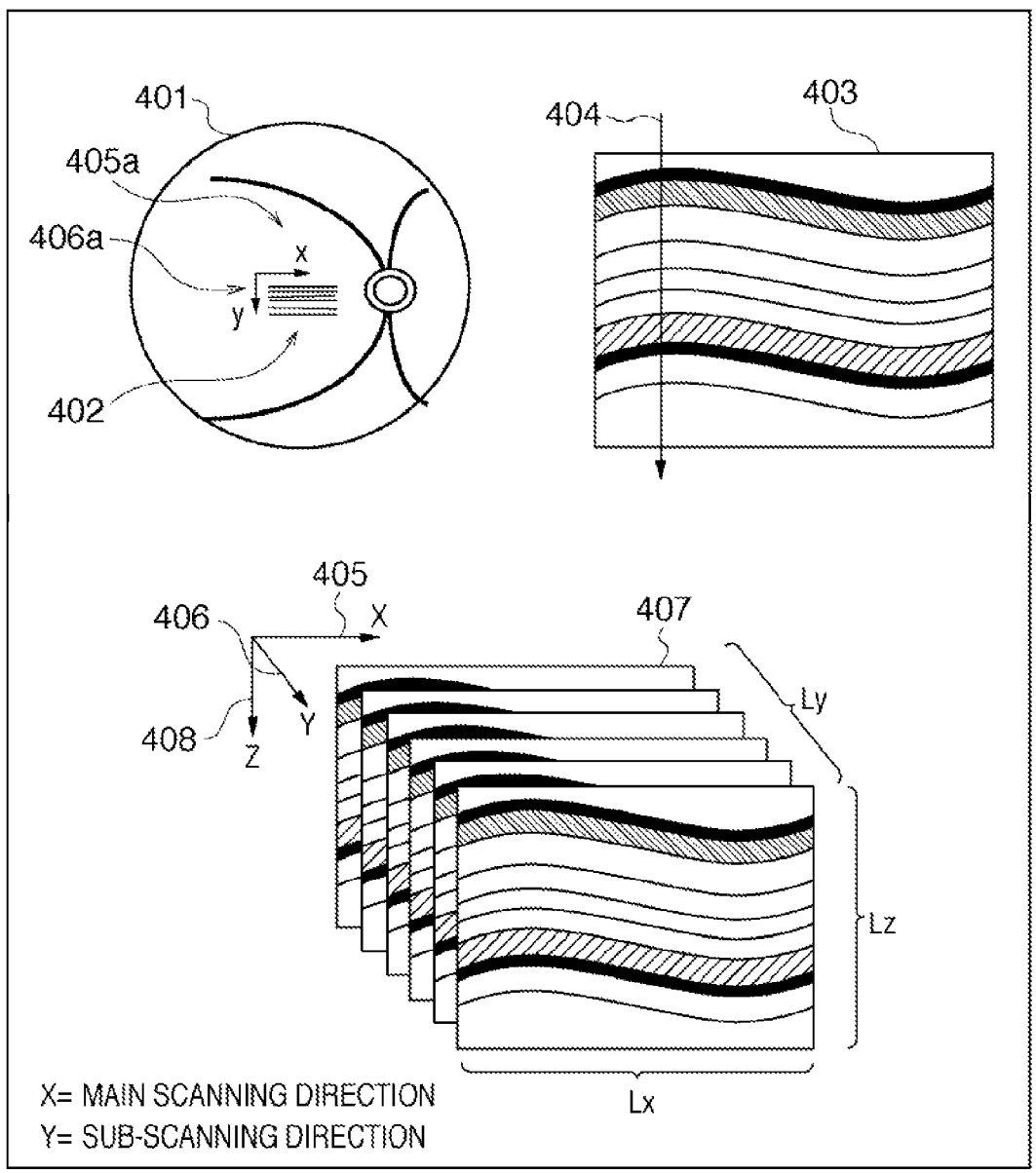
FIG. 4 is a view showing a reconstructed three-dimensional tomogram.

FIG. 4 is a view showing an example of a three-dimensional tomogram reconstructed by making the tomogram acquisition unit 110 start imaging. Referring to FIG. 4, reference numeral 401 denotes an example of the fundus retina of an object; 403, an example of a two-dimensional tomogram of the fundus retina 401 generated by the tomogram acquisition unit 110; 405a or 405, a main scanning direction (X-axis direction); 406a or 406, a sub-scanning direction (Y-axis direction); and 408, the depth direction (Z-axis direction) of an A-scan signal.

The tomogram acquisition unit 110 generates the two-dimensional tomogram 403 shown in FIG. 4 by making the signal processing unit 210 reconstruct A-scan signals 404 one by one while moving the galvanometer mirror 205 in the main scanning direction. The two-dimensional tomogram 403 is called a "B-scan image", which is a two-dimensional tomogram at a two-dimensional slice in the depth direction relative to the fundus retina 401 and a direction (X-axis direction) perpendicular to the depth direction, that is, a plane defined by the X-axis direction 405 and the Z-axis direction 408 shown in FIG. 4. Reference numeral 402 denotes the imaging position of the two-dimensional tomogram 403.

Continuously shifting the imaging position 402 of a B-scan image in the sub-scanning direction (Y-axis direction) (scanning in the sub-scanning direction) will obtain a B-scan image at each imaging position 402. Reference numeral 407 denotes a three-dimensional tomogram constituted by the B-scan images captured at the respective imaging position in the sub-scanning direction. Generating a plurality of B-scan images at the imaging positions 402 in the sub-scanning direction in this manner will generate a three-dimensional tomogram. Referring to FIG. 4, reference symbol Ly denotes the number of B-scan images corresponding to an imaging range; Lx, the number of A-scan signals constituting a B-scan image; and Lz, the sampling number of A-scan signals.

The three-dimensional tomogram 407 (a plurality of B-scan images) generated by the tomogram acquisition unit 110 is transmitted to the tomogram analysis unit 120 and the storage unit 130.

In step S330, the tomogram analysis unit 120 extracts feature amounts used for positional offset correction of B-scan images.

In the case of a three-dimensional tomogram of the fundus retina 401, an anatomical structure of the fundus retina 401 is captured as a B-scan image. That is, the apparatus can correct positional offsets between B-scan images by extracting feature amounts associated with the shape structure of the tissue of the fundus retina 401 from B-scan images and correcting the positions of the B-scan images so as to maintain the continuity of the shape structure based on the feature amounts. The feature amount extraction processing in step S330 will be described by taking a blood vessel as an example of the shape structure of the tissue of the fundus retina 401.

Figure 5:
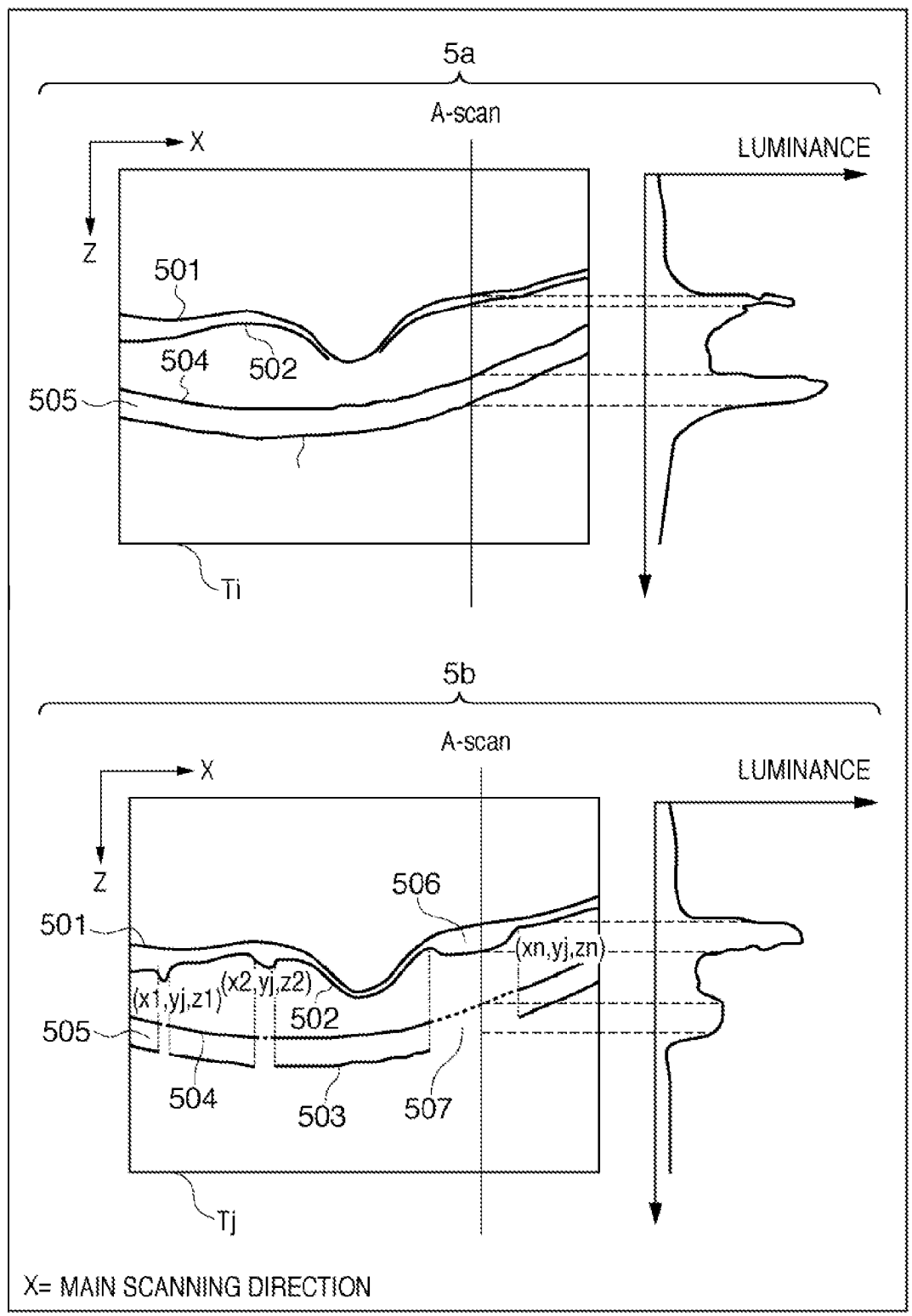
FIG. 5 is a view showing an example of B-scan images constituting a three-dimensional tomogram.

5a of FIG. 5 shows an example of a B-scan image Ti of the three-dimensional tomogram 407 and an A-scan signal at a position on the B-scan image Ti at which no blood vessel exists. 5b of FIG. 5 shows an example of a B-scan image Tj of the three-dimensional tomogram 407 and an A-scan signal at a position on the B-scan image Tj at which a blood vessel exists.

Referring to the B-scan images Ti and Tj, reference numeral 501 denotes an internal limiting membrane; 502, a nerve fiber layer boundary; 503, a retinal pigment epithelium; 504, the junction between the photoreceptor inner and outer segments; 505, a stratum neuroepitheliale; 506, a blood vessel region; and 507, a region below a blood vessel.

As indicated by 5b of FIG. 5, in the presence of a blood vessel, the region 507 below the blood vessel in the B-scan image Tj has a low luminance as a whole because of the shadow of the blood vessel. This leads to high contrast relative to the neighboring luminances. In consideration of such a characteristic of a B-scan image, this embodiment extracts the position of an A-scan signal (the position in the X-axis direction) at which a contrast change has occurred, as a feature amount associated with the shape structure of the tissue in the B-scan image, from the B-scan image.

More specifically, the tomogram analysis unit 120 calculates a change amount g(i, j, k) of contrast relative to each B-scan image constituting the three-dimensional tomogram 407 based on equation (1) given below.

$$g(i, j, k) = \sqrt{\{f(i+1, j, k) - f(i, j, k)\}^2 \times wx + \{f(i, j+1, k) - f(i, j, k)\}^2 \times wz} \quad (1)$$

for $i = 0, 1, \ldots, L_x - 1$ $j = 0, 1, \ldots, L_z - 1$ $k = 0, 1, \ldots, L_y - 1$ $wx \geq 0$ $wz \geq 0$ In equation (1), f(i, j, k) represents the pixel value at a position (i, j, k) on the three-dimensional tomogram 407, Lx is the number of pixels of the three-dimensional tomogram 407 in the X-axis direction 405 (i.e., the number of A-scan signals), Lz is the number of pixels in the Z-axis direction 408 (i.e., the sampling number of A-scan signals), Ly is the number of pixels in the Y-axis direction 406 (i.e., the number of B-scan signals), and wx and wz are weights for change amounts of contrast in the X-axis direction 405 and the Z-axis direction 408. In this case, wx=1 and wz=1. However, when the change amount of contrast in either of the directions is to be preferentially used, the weight in the direction in which the change amount of contrast is preferentially used is increased. If, for example, the change amount of contrast between the region 507 below the blood vessel and the surrounding region is to be preferentially used, wz>>wx (e.g., wz=10 and wx=0.1).

This embodiment will exemplify a case in which change amounts of contrast are used as feature amounts. However, the feature amounts to be used are not limited to change amounts of contrast as long as there is a spatial difference from the surrounding region within a B-scan image, and the difference allows specification of the position of the B-scan image.

For example, it is possible to use an edge intensity in a B-scan image as a feature amount. In this case, an edge intensity is calculated by using a Laplacian filter, Sobel filter, Canny filter, or the like. It is also possible to use a spatial frequency of a B-scan image as another feature amount.

In addition, when correcting the positional offsets between the respective B-scan images of the three-dimensional tomogram 407 of the fundus retina 401, this embodiment pays attention to the blood vessel in the fundus retina 401. However, the present invention is not limited to this. For example, since the shape structure of a lesion such as a leukoma influences the change amount of contrast in a B-scan image, it is possible to pay attention to the shape structure of a lesion such as a leukoma.

The storage unit 130 stores the feature amount g(i, j, k) extracted by the tomogram analysis unit 120.

In step S340, the tomogram selection unit 140 compares the feature amounts extracted from the respective B-scan images to search for a B-scan image having a large feature amount, and selects it as a standard tomogram for position correction. More specifically, first of all, the tomogram selection unit 140 calculates a value P(k) by adding up change amounts g of contrast extracted from the respective B-scan images constituting the three-dimensional tomogram 407 in step S330, based on equation (2) given below.

$$P(k) = \sum_{i=0}^{i \leq L_x - 1} \sum_{j=0}^{j \leq L_z - 1} g(i, j, k) \quad (2)$$

$$0 \leq k < Ly$$

where P(k) is the accumulated value of the change amounts g of contrast of a kth B-scan image B(k).

The tomogram selection unit 140 obtains an rth (r is an integer equal to or more than 1) B-scan image B(r) having a maximum value P( ) based on equation (3) given below.

$$P(r) = \underset{k}{\operatorname{argmax}}(P(k)) \quad (3)$$

The tomogram selection unit 140 then selects the rth B-scan image B(r) as a standard tomogram. A number r of the B-scan image selected as a standard tomogram is stored in the storage unit 130 and transferred to the tomogram position correction unit 150.

In step S350, the tomogram position correction unit 150 corrects the positional offset between the standard tomogram B(r) selected in step S340 and a B-scan image adjacent to the standard tomogram B(r). The tomogram position correction unit 150 then sequentially repeats positional offset correction for adjacent B-scan images. This will correct the positional offsets between the respective B-scan images constituting the three-dimensional tomogram 407. Note that a procedure for tomogram position correction processing which repeats positional offset correction using the standard tomogram B(r) will be described in detail later.

The three-dimensional tomogram 407 having undergone positional offset correction by the tomogram position correction unit 150 is constituted by the respective B-scan images and their position correction values (x, z), that is, position correction values within the X-Z planes of the respective B-scan images.

Although this embodiment has exemplified the position correction values (x, z) within the X-Z planes, the embodiment may be configured to calculate position correction values (x, y, z) of B-scan images (k) by using equation (4) given below.

$$S(k) = (x, y, z) \quad (4)$$

where S(k) is the position correction values (x, y, z) of the kth B-scan image (in this embodiment, since no positional offset correction is performed in the Y-axis direction, y is 0).

In step S360, the storage unit 130 stores the three-dimensional tomogram 407 having undergone positional offset correction. Note that this apparatus may be configured to transfer the three-dimensional tomogram 407 having undergone positional offset correction to an external data server (not shown) via the tomogram output unit 160 and store the tomogram in the external data server.

In step S370, the tomography apparatus 100 determines whether it has received an instruction to end the tomography/correction processing. Assume that the operator inputs an instruction to end tomography/correction processing via a keyboard or mouse (not shown). If the apparatus determines in step S370 that it has received an instruction to end the tomography/correction processing, the apparatus terminates the tomography/correction processing. If the apparatus determines that it has not received an instruction to end the tomography/correction processing, the process returns to step S310 to execute tomography/correction processing for the fundus retina of the next object (or execute tomography/correction processing again for the fundus retina of the same object).

4. Explanation of Tomogram Position Correction Processing

Figure 6:
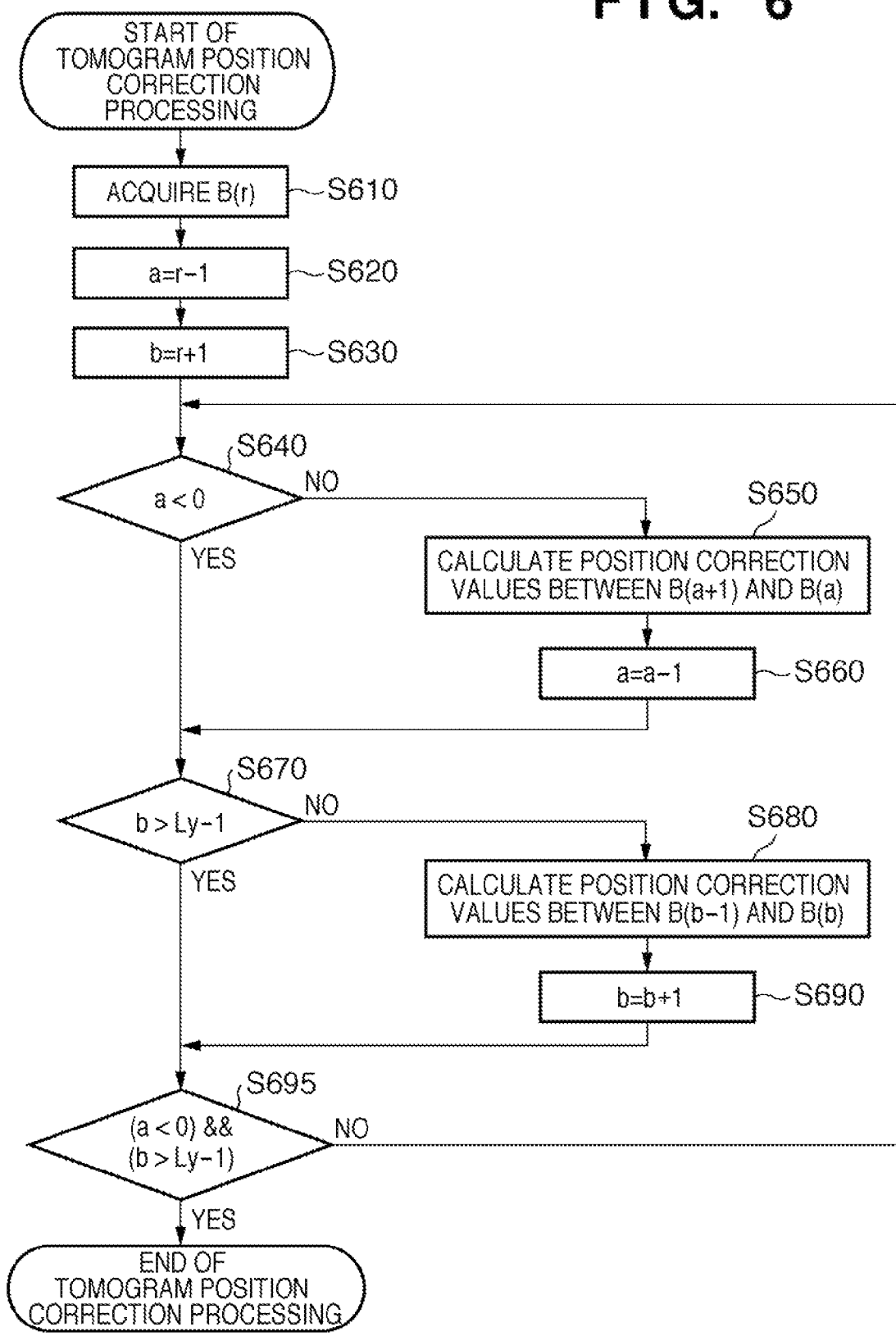
FIG. 6 is a flowchart showing the details of tomogram position correction processing.

A procedure for tomogram position correction processing (step S350) executed by the tomogram position correction unit 150 will be described in detail next with reference to FIG. 6.

In step S610, the tomogram position correction unit 150 acquires the standard tomogram B(r) selected in step S340.

In step S620, the tomogram position correction unit 150 substitutes r−1 into a number a specifying a B-scan image adjacent to the acquired standard tomogram B(r).

In step S630, the tomogram position correction unit 150 substitutes r+1 into a number b specifying a B-scan image adjacent to the acquired standard tomogram B(r).

In step S640, the tomogram position correction unit 150 determines whether an ath B-scan image B(a) exists. If the tomogram position correction unit 150 determines that the image exists, the process advances to step S650. If the tomogram position correction unit 150 determines that the B-scan image B(a) does not exist, the process advances to step S670.

In step S650, the tomogram position correction unit 150 calculates position correction values for correcting the relative positional offsets between the B-scan image B(a) and a B-scan image B(a+1) in the X-axis direction and the Z-axis direction.

Note that the tomogram position correction unit 150 calculates position correction values between adjacent B-scan images by determining a region of interest (to be referred to as an ROI hereafter) and searching for the same pattern in the adjacent B-scan images by using a pattern matching method. This embodiment uses the SSD (Sum of Squares Difference) represented by equation (5) as a similarity in pattern matching.

$$SSD = \frac{1}{N} \sum_i \sum_j (C(i, j) - D(i, j))^2 \quad (5)$$

In equation (5), C and D are the pixel values of ROIs of the adjacent B-scan images B(a+1) and B(a), i and j are the position of pixels in the ROIs, and N is the total number of pixels in each ROI.

The tomogram position correction unit 150 then searches for a position at which the SSD becomes minimum while translating the ROI in the B-scan image (a) relative to the adjacent B-scan image (a+1), that is, moving the ROI in the X-axis direction and the Z-axis direction. The tomogram position correction unit 150 sets the positional offset amounts at the position at which the SSD becomes minimum as position correction values (x, z) for the adjacent B-scan image (a+1).

Note that the size of an ROI is determined in consideration of an imaging range, the size of a measurement target, and the like. For example, the size may be a fixed value such as 128×128 pixels or a variable value such as ⅔ the center of an entire B-scan image.

Although this embodiment calculates position correction values by using an SSD, the present invention is not limited to this and may calculate position correction values for a B-scan image by using other known techniques such as a mutual information content method and a cross-correlation coefficient method.

The calculated position correction values (x, z) are added to the B-scan image B(a) and stored in the storage unit 130.

In step S660, the tomogram position correction unit 150 calculates a=a−1 to set the next B-scan image as a target for the calculation of position correction values.

In step S670, the tomogram position correction unit 150 determines whether a bth B-scan image B(b) exists. If the tomogram position correction unit 150 determines that the image exists, the process advances to step S680. If the tomogram position correction unit 150 determines that the B-scan image B(b) does not exist, the process advances to step S695.

In step S680, the tomogram position correction unit 150 calculates position correction values for the B-scan image B(b) and a B-scan image B(b−1) in the X-axis direction and the Z-axis direction. This calculation of position correction values is the same as that performed in step S650, and hence a description of the calculation will be omitted.

The calculated position correction values (x, z) are added to the B-scan image B(b) and stored in the storage unit 130.

In step S690, the tomogram position correction unit 150 calculates b=b+1 to set the next B-scan image as a target for the calculation of position correction values.

In step S695, the tomogram position correction unit 150 determines whether the calculation of position correction values is complete for all the B-scan images constituting the three-dimensional tomogram 407. If the tomogram position correction unit 150 determines that there is a B-scan image for which no position correction values have been calculated, the process returns to step S640. If the tomogram position correction unit 150 determines that the calculation of position correction values is complete for all the B-scan images constituting the three-dimensional tomogram 407, the unit terminates the tomogram position correction processing.

Note that this embodiment is configured to add position correction values (x, y, z) to the respective B-scan images B(y) and store the resultant information. However, the present invention is not limited to this and may be configured to perform positional offset correction for each pixel (x, z) of each B-scan image (X-Z plane) and store the B-scan images B(y) having undergone positional offset correction.

This embodiment is configured to make the tomogram acquisition unit 110 acquire a three-dimensional tomogram and execute tomogram position correction processing. However, the present invention is not limited to this, and may be configured to read out a three-dimensional tomogram stored in advance in the storage unit 130 or a three-dimensional tomogram stored in a data server (not shown) and execute tomogram position correction processing.

As is obvious from the above description, the tomography apparatus according to this embodiment is configured to select, as a standard B-scan image, one of a plurality of B-scan images constituting a three-dimensional tomogram which has a large accumulated value of feature amounts associated with the shape structure of the tissue. The apparatus is also configured to perform positional offset correction for the selected B-scan image and an adjacent B-scan image by pattern matching so as to make the adjacent B-scan image match the selected B-scan image (so as to maintain the continuity of the shape structure). The apparatus is further configured to perform positional offset correction for the B-scan image having undergone positional offset correction and an adjacent B-scan image so as to make the adjacent B-scan image match the B-scan image having undergone positional offset correction (so as to maintain the continuity of the shape structure). Repeating such positional offset correction in this manner will correct all positional offsets between a plurality of B-scan images constituting a three-dimensional tomogram.

Consequently, according to this embodiment, it is possible to implement accurate positional offset correction.

Second Embodiment

The first embodiment is configured to perform positional offset correction between the respective B-scan images constituting a three-dimensional tomogram by using a B-scan image as a standard tomogram. However, the standard tomogram to be used is not limited to a B-scan image. For example, when simultaneously capturing a plurality of three-dimensional tomograms by simultaneously applying a plurality of measurement light beams which are scanned in conjunction with each other (integrally), one of the three-dimensional tomograms may be selected as a standard tomogram. Assume that in this case, the method described in the first embodiment is used to correct positional offsets between the respective B-scan images constituting a three-dimensional tomogram selected as a standard tomogram (standard three-dimensional tomogram). Assume also that the positional offset correction is performed for three-dimensional tomograms other than the standard three-dimensional tomogram by using the relative positional relationship between the irradiation positions of a plurality of measurement light beams based on the standard three-dimensional tomogram having undergone positional offset correction. This embodiment will be described in detail below.

Since the basic arrangement of a tomography apparatus according to this embodiment is the same as that of the tomography apparatus 100 described with reference to FIG. 1 in the first embodiment, a description of the arrangement will be omitted. Note however, that the second embodiment differs from the first embodiment in the detailed arrangement of a tomogram acquisition unit. For this reason, the detailed arrangement of the tomogram acquisition unit will be described below. In addition, the differences in tomography/correction processing and tomogram position correction processing between the embodiments due to the difference between the detailed arrangements of the tomogram acquisition units will be described.

<1. Detailed Arrangement of Tomogram Acquisition Unit>

Figure 7:
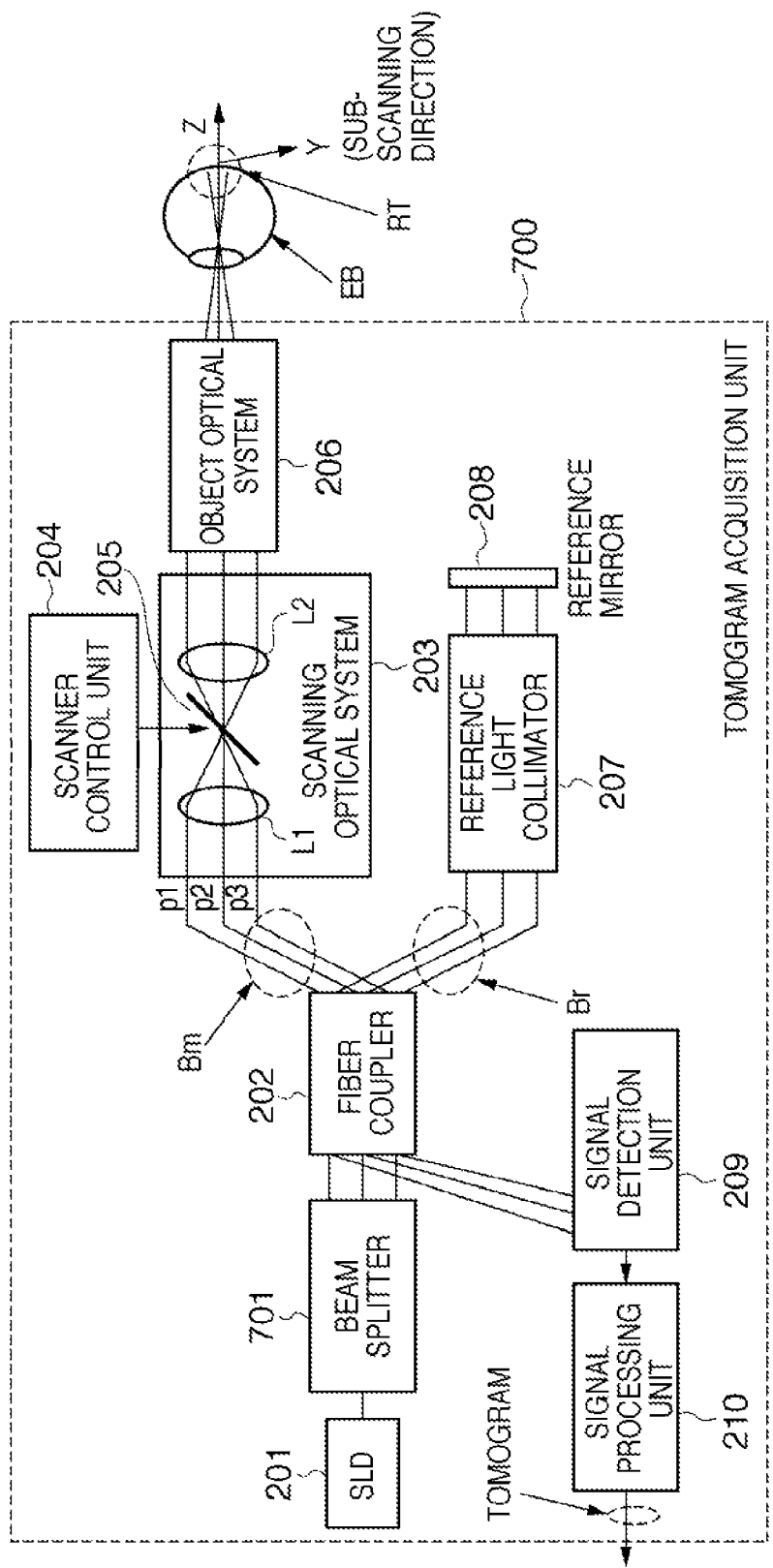
FIG. 7 is a block diagram showing the detailed arrangement of a tomogram acquisition unit.

FIG. 7 is a block diagram showing the detailed arrangement of a tomogram acquisition unit 700 of the tomography apparatus 100 according to this embodiment. As shown in FIG. 7, in the tomogram acquisition unit 700, a beam splitter 701 splits light emitted by an SLD 201 as a low-coherence light source into three light beams, which then strike a fiber coupler 202. The fiber coupler 202 separates the incident light beams into measurement light beams Bm and reference light beams Br. Of these light beams, the measurement light beams Bm strike a scanning optical system 203 through optical fibers, and the reference light beams Br strike a reference light collimator 207 through optical fibers.

The scanning optical system 203 includes a lens L1, and focuses the incident measurement light beams Bm on a galvanometer mirror 205. The galvanometer mirror 205 scans a fundus retina RT as a measurement target with the focused measurement light beams Bm.

Assume that the scanning optical system 203 is configured to make a measurement light arrangement changing unit (not shown) arbitrarily change the incident light arrangement of three measurement light beams constituting the incident measurement light beams Bm with respect to the fundus retina RT.

Figure 8:
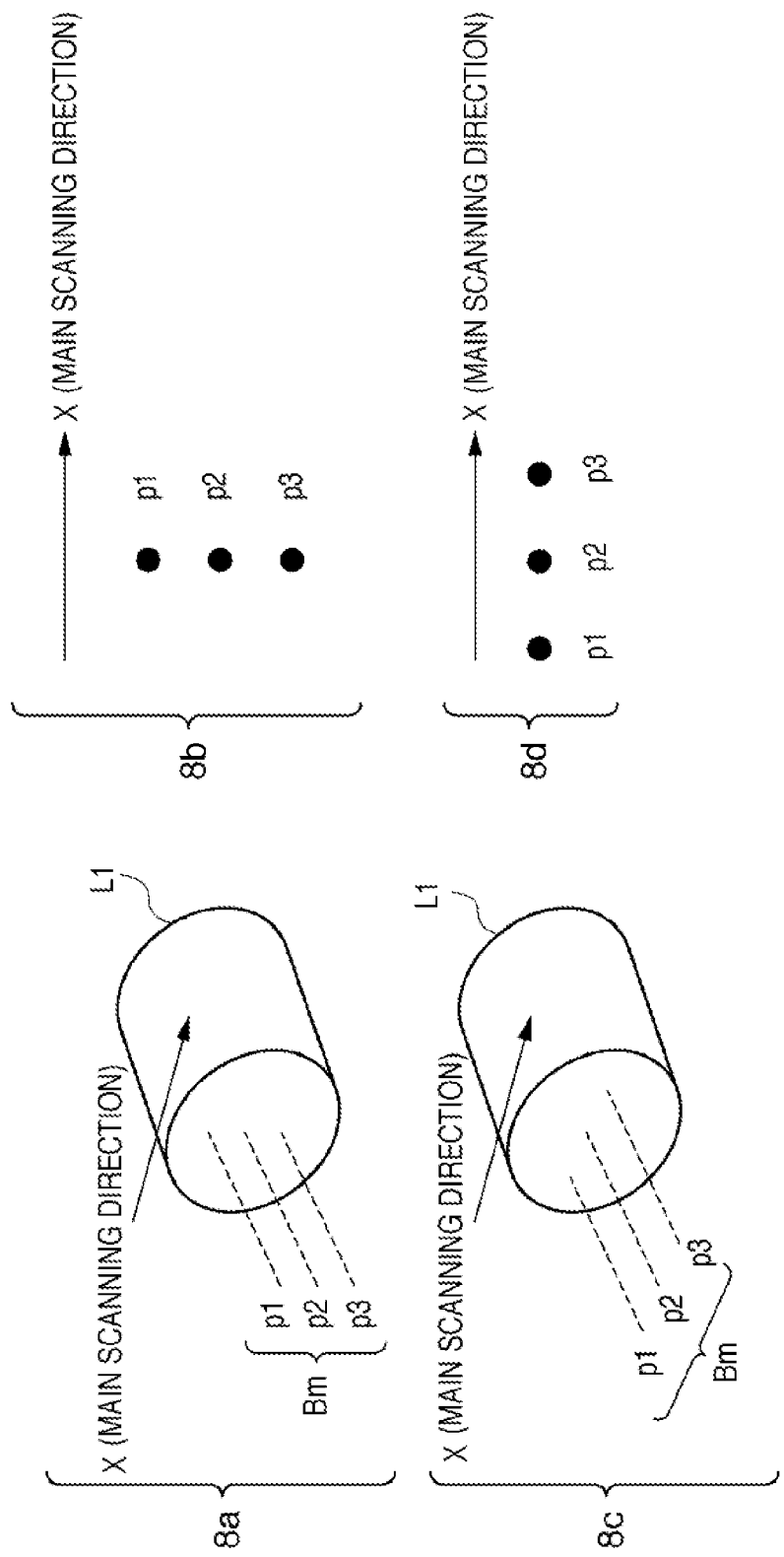
FIG. 8 is a view showing the arrangement of measurement light beams.

FIG. 8 is a view showing the incident light arrangement of the measurement light beams Bm which have struck the scanning optical system 203. Reference numeral 8a of FIG. 8 indicates a case in which three measurement light beams p1, p2, and p3 constituting the measurement light beams Bm strike the scanning optical system 203 vertically relative to the main scanning direction. Reference numeral 8c of FIG. 8 indicates a case in which the measurement light beams strike the scanning optical system 203 horizontally relative to the main scanning direction. Reference numerals 8b and 8d of FIG. 8 each indicate the arrangement of the measurement light beams p1 to p3 on the fundus retina RT in the main scanning direction.

Referring back to FIG. 7, the galvanometer mirror 205 has two drive shafts. A scanner control unit 204 controls the galvanometer mirror 205 through the drive shafts so as to scan the measurement light beams Bm on the fundus retina RT in the main scanning direction and the sub-scanning direction.

The measurement light beams Bm output from the galvanometer mirror 205 reach the fundus retina RT as a measurement target through a lens L2 and an object optical system 206. The light beams are then reflected by the fundus retina RT and reach the fiber coupler 202 through the object optical system 206 and the scanning optical system 203.

On the other hand, the reference light beams Br output from the fiber coupler 202 are guided to a reference mirror 208 through the optical fibers and the reference light collimator 207. The light beams are reflected by the reference mirror 208 and reach the fiber coupler 202 again to cause interference with the three measurement light beams constituting the measurement light beams Bm reflected by the fundus retina RT, thereby generating three interference light beams. The generated three interference light beams are input to a signal detection unit 209.

The signal detection unit 209 detects the three interference light beams and converts them into electrical signals. The signal detection unit 209 then outputs the signals as three interference signals to a signal processing unit 210. The signal processing unit 210 generates three A-scan signals corresponding to the reflectances at the respective portions on the fundus retina RT in the Z-axis direction by performing signal processing such as Fourier transformation for the three interference signals.

Figure 9:
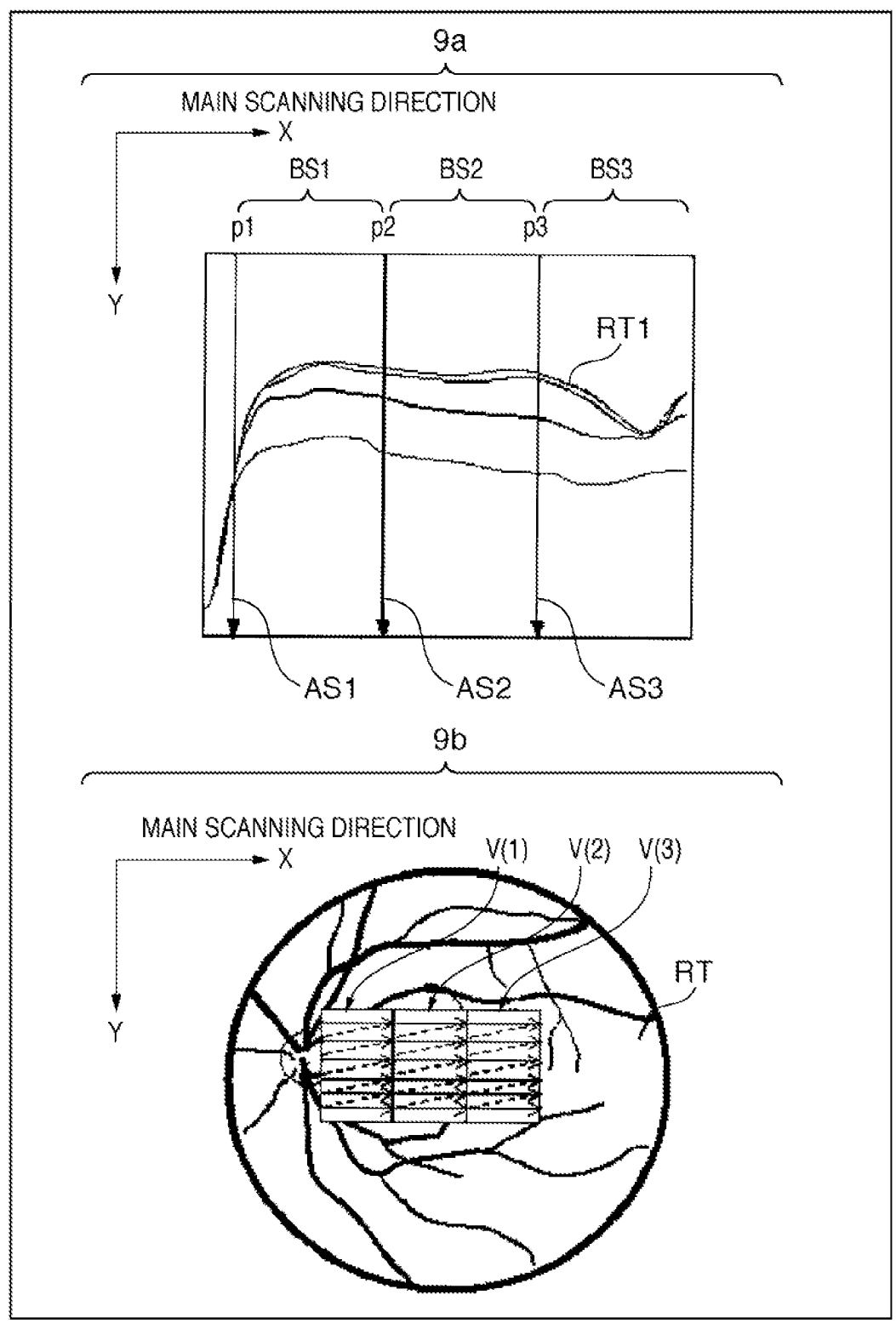
FIG. 9 is a view showing the relationship between a generated A-scan signal and the fundus retina.

FIG. 9 is a view showing three A-scan signals AS1, AS2, and AS3 generated based on the three measurement light beams Bm in the horizontal arrangement indicated by 8c of FIG. 8, together with the fundus retina RT.

As indicated by 9a of FIG. 9, the tomogram acquisition unit 700 generates the A-scan signals AS1, AS2, and AS3 while scanning the plurality of measurement light beams p1 to p3 in the main scanning direction, thereby generating B-scan images BS1, BS2, and BS3 respectively corresponding to the A-scan signals AS1, AS2, and AS3.

Reference symbols V(1), V(2), and V(3) in 9b of FIG. 9 respectively denote three-dimensional tomograms generated based on the measurement light beams p1, p2, and p3, and also denote imaging ranges on the fundus retina RT.

In this case, the relative positional relationship (offset amounts) between the A-scan signals AS1, AS2, and AS3 generated based on the respective measurement light beams on the fundus retina RT are known. For this reason, letting a and b be imaging positions on the fundus retina RT (i.e., the irradiation positions of the respective measurement light beams), equations (6) and (7) hold.

$$XPas(b,t)=XPas(a,t)+\Delta x(a,b) \quad (6)$$

$$YPas(b,t)=YPas(a,t)+\Delta y(a,b) \quad (7)$$

for
a, b={AS1, AS2, AS3}
a≠b where Xpas(b, t) is the X coordinate of the imaging position b on the retina at time t, Ypas(b, t) is the Y coordinate of the imaging position b on the retina at time t, $\Delta x(a, b)$ is the relative positional relationship between b and a in the X direction, and $\Delta y(a, b)$ is the relative positional relationship between b and a in the Y direction.

In the above equations, $\Delta x(a, b)$ and $\Delta y(a, b)$ also represent the relative positional relationship (offset amounts) in the imaging ranges of an A-scan signal a and A-scan signal b.

<2. Explanation of Tomography/Correction Processing>

Figure 10:
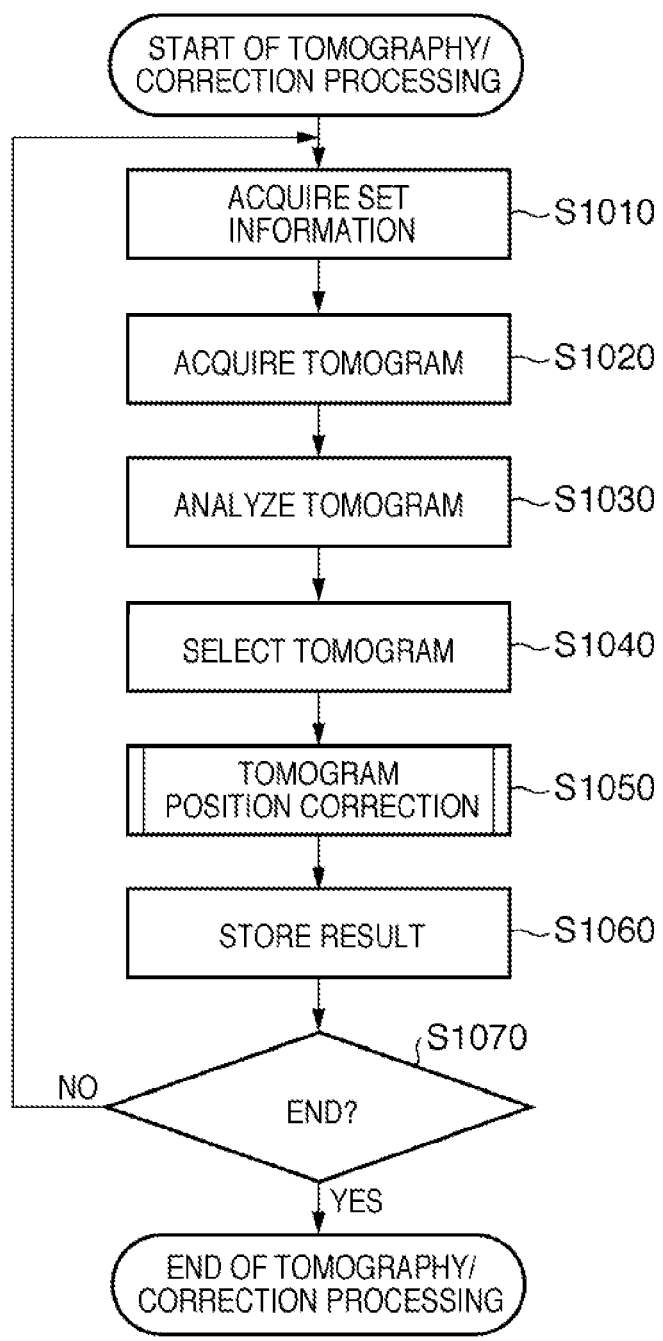
FIG. 10 is a flowchart showing a procedure for tomography/correction processing.

A procedure for tomography/correction processing in the tomography apparatus according to this embodiment will be described next. FIG. 10 is a flowchart showing a procedure for tomography/correction processing in the tomography apparatus according to the embodiment.

As shown in FIG. 10, when starting tomography/correction processing, the apparatus acquires various kinds of set information input by the operator via a keyboard, a mouse, and the like (not shown) in step S1010, and transmits the information to the tomogram acquisition unit 700.

Note that since set information has been described in detail in the first embodiment, a description of the information will be omitted. Note however that the tomography apparatus according to this embodiment acquires instructions designating the number of measurement light beams (e.g., "3"), the arrangement of measurement light beams (e.g., "horizontal arrangement"), and the like, in addition to the set information described in the first embodiment, and transmits the pieces of information to the tomogram acquisition unit 700.

In step S1020, a tomogram acquisition unit 110 starts capturing a three-dimensional tomogram based on the transmitted set information.

Note that since the three-dimensional tomogram reconstructed by the tomogram acquisition unit 700 has already been described with reference to FIG. 4 in the first embodiment, a description of the tomogram will be omitted. Note however that the tomography apparatus according to this embodiment concurrently reconstructs three three-dimensional tomograms based on three A-scan signals. Three tomograms V(1), V(2), and V(3) generated by the tomogram acquisition unit 700 are transmitted to a tomogram analysis unit 120 and a storage unit 130.

In step S1030, the tomogram analysis unit 120 extracts feature amounts used for positional offset correction for the B-scan images constituting each three-dimensional tomogram. Note that since the extraction of feature amounts has already been described in detail in the first embodiment, a description of the extraction will be omitted. The storage unit 130 stores the feature amounts extracted by the tomogram analysis unit 120.

In step S1040, a tomogram selection unit 140 compares the feature amounts extracted from the respective B-scan images for each three-dimensional tomogram to search for a three-dimensional tomogram having a large accumulated value of feature amounts, thereby selecting a standard three-dimensional tomogram.

More specifically, the tomogram selection unit 140 calculates a value P(w) by adding up change amounts g of contrast extracted in step S1030 from the respective B-scan images constituting each three-dimensional tomogram acquired in step S1010, based on equation (8) given below. Note that w represents the wth three-dimensional tomogram (0<=w<Lw), and P(w) represents the accumulated value of change amounts g(i, j, k) of contrast of the wth three-dimensional tomogram.

$$P(w) = \sum_{k=0}^{k<L_y} \sum_{i=0}^{i \leq L_x-1} \sum_{j=0}^{j \leq L_z-1} g(i, j, k)_w \qquad (8)$$

$$0 \leq w < Lw$$

where Lw is the number of three-dimensional tomograms. In this embodiment, Lw=3.

The tomogram selection unit 140 then obtains an rth three-dimensional tomogram V(r) having a maximum value P( ) based on equation (9) given below.

$$P(r) = \operatorname*{argmax}_{w}(P(w)) \qquad (9)$$

The tomogram selection unit 140 then selects the rth three-dimensional tomogram as a standard three-dimensional tomogram. A number r of the three-dimensional tomogram selected as a standard three-dimensional tomogram is stored in the storage unit 130 and transferred to a tomogram position correction unit 150.

In step S1050, the tomogram position correction unit 150 performs positional offset correction for the respective B-scan images constituting the standard three-dimensional tomogram V(r) selected in step S1040. The tomogram position correction unit 150 then performs positional offset correction for three-dimensional tomograms other than the standard three-dimensional tomogram V(r) based on the relative positional relationship between them and the standard three-dimensional tomogram V(r) (a procedure for tomogram position correction processing will be described in detail later).

The tomogram position correction unit 150 performs positional offset correction for the standard three-dimensional tomogram V(r) first in this manner for the following reason. As described in the first embodiment, in the case of a three-dimensional tomogram of the fundus retina, the anatomical structure of the fundus retina is captured as a B-scan image. On the other hand, the layered structure of the fundus retina has a characteristic that it exhibits many changes in the Z-axis direction but few changes in the X-axis direction. For this reason, a three-dimensional tomogram from which feature amounts associated with the shape structure of the retinal tissue exhibiting many changes in the X-axis direction are extracted can be a three-dimensional tomogram which allows positional offset correction most accurately. In other words, the three-dimensional tomogram selected in step S1040 (i.e., the standard three-dimensional tomogram) is a three-dimensional tomogram, of the plurality of three-dimensional tomograms, which allows most accurate positional offset correction. On the other hand, in this embodiment, positional offset correction is performed for three-dimensional tomograms other than the three-dimensional tomogram having undergone positional offset correction first, based on the relative positional relationship. That is, accurately performing the first positional offset correction will lead to accurate positional offset correction of other three-dimensional positional offsets. For this reason, positional offset correction is performed first for the standard three-dimensional tomogram V(r).

Referring back to FIG. 10, in step S1060, the storage unit 130 stores the three-dimensional tomograms having undergone positional offset correction.

In step S1070, the tomography apparatus 100 determines whether it has received an instruction to end the tomography/correction processing. Assume that the operator inputs an instruction to end tomography/correction processing via a keyboard or mouse (not shown). If the apparatus determines in step S1070 that it has received an instruction to end the tomography/correction processing, the apparatus terminates the tomography/correction processing. If the apparatus determines that it has accepted no instruction to end the tomography/correction processing, the process returns to step S1010 to execute tomography/correction processing for the fundus retina of the next object (or execute tomography/correction processing again for the fundus retina of the same object).

<3. Explanation of Tomogram Position Correction Processing>

Figure 11:
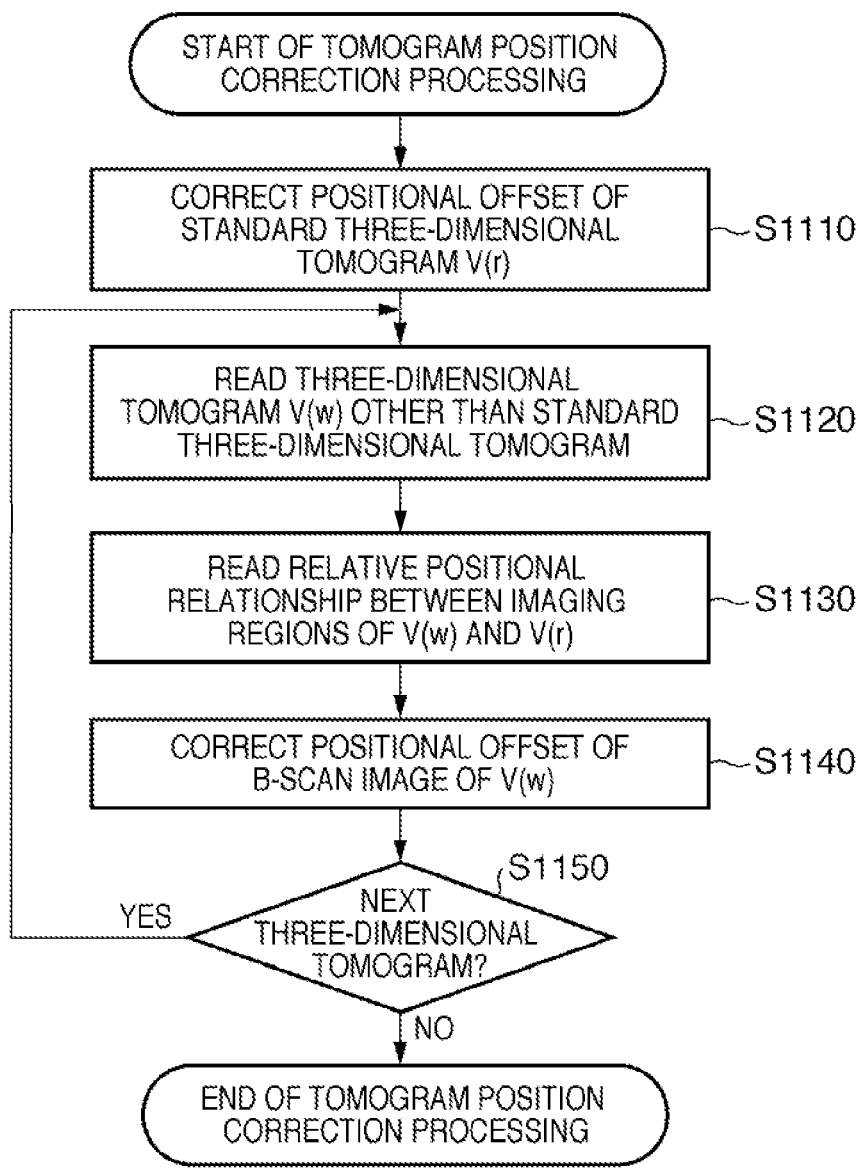
FIG. 11 is a flowchart showing a procedure for tomogram position correction processing.

A procedure for tomogram position correction processing (step S1050) in this embodiment will be described in detail next with reference to FIG. 11.

In step S1110, this apparatus acquires the standard three-dimensional tomogram V(r) selected in step S1040, and performs positional offset correction between the respective B-scan images constituting the standard three-dimensional tomogram V(r). The operation of the tomography apparatus for positional offset correction between the respective B-scan images constituting the standard three-dimensional tomogram V(r) is the same as that of the tomography apparatus which is indicated by steps S310 to S360 described with reference to FIG. 3 in the first embodiment. For this reason, a description of the operation will be omitted.

In step S1120 and the subsequent steps, the apparatus performs positional offset correction for three-dimensional tomograms other than the standard three-dimensional tomogram V(r) by using the positional offset correction result on the standard three-dimensional tomogram V(r) in step S1110. Note that when positional offset correction is to be performed in the above manner, the relative positional relationship (offset amounts) between the irradiation positions of the respective measurement light beams on the fundus retina is known in advance.

In step S1120, the apparatus reads a three-dimensional tomogram V(w) other than the standard three-dimensional tomogram V(r) selected in step S1040 from the storage unit 130.

In step S1130, the apparatus reads the three-dimensional tomogram V(w), the standard three-dimensional tomogram V(r), and relative positional relationships $\Delta x(r, w)$ and $\Delta y(r, w)$ concerning irradiation positions from the storage unit 130.

In step S1140, the apparatus performs positional offset correction for the B-scan images of the three-dimensional tomogram V(w) by using the positional offset correction result on the respective B-scan images of the standard three-dimensional tomogram V(r) based on equation (10).

$$S(w,k) = S(r,k) + (\Delta x(r,w), \Delta y(r,w), \Delta z(r,w)) \quad (10)$$

where k represents the kth B-scan image of the three-dimensional tomogram ($0 \leq k < Ly$), and $\Delta x(r, w)$, $\Delta y(r, w)$, and $\Delta z(r, w)$ represent the relative positional relationship (offset amounts) between the irradiation positions of the respective measurement light beams applied when the standard three-dimensional tomogram V(r) and the three-dimensional tomogram V(w) are generated. Note that in this embodiment, $\Delta z(r, w) = 0$.

In step S1150, the apparatus determines whether there is any three-dimensional tomogram which has not undergone positional offset correction. If the apparatus determines in step S1150 that there is such a tomogram, the process return to step S1120. If the apparatus determines that positional offset correction is complete for all the three-dimensional tomograms, the apparatus terminates the tomogram position correction processing.

As is obvious from the above description, the tomography apparatus according to this embodiment is configured to select a standard three-dimensional tomogram suitable for positional offset correction from a plurality of three-dimensional tomograms obtained by concurrently performing imaging using a plurality of measurement light beams. The apparatus is configured to perform the same positional offset correction as that in the first embodiment for the B-scan images constituting the standard three-dimensional tomogram. The apparatus is also configured to perform positional offset correction for three-dimensional tomograms other than the standard three-dimensional tomogram by using the positional offset correction result on the standard three-dimensional tomogram based on the relative positional relationship.

As a consequence, it is possible to accurately correct the positional offsets between a plurality of B-scan images of a three-dimensional tomogram.

Third Embodiment

The second embodiment is configured to select one standard three-dimensional tomogram suitable for positional offset correction. In general, however, the feature amounts in a three-dimensional tomogram are not uniform, and are offset in value. For this reason, the accuracy of positional offset correction may degrade in a region having a small feature amount even in a standard three-dimensional tomogram. A standard three-dimensional tomogram may include a region exhibiting a smaller feature amount than a corresponding region in another three-dimensional tomogram.

This embodiment therefore segments each of a plurality of three-dimensional tomograms into a plurality of regions, selects a region exhibiting a large feature amount as a standard region tomogram, and performs positional offset correction for corresponding regions in other three-dimensional tomograms based on the standard region tomogram.

Since the basic arrangement of a tomography apparatus according to this embodiment is the same as that of the tomography apparatus described with reference to FIG. 1 in the first embodiment, a description of the arrangement will be omitted. In addition, since a procedure for tomography/correction processing in the tomography apparatus according to the first embodiment is basically the same as that in the second embodiment, different points (steps S1040 and S1050) will be described below.

<Tomography/Correction Processing>

In step S1040, a tomogram selection unit 140 searches regions corresponding to a plurality of three-dimensional tomograms for a standard region tomogram exhibiting a largest feature amount.

More specifically, first of all, the tomogram selection unit 140 segments each of generated three-dimensional tomograms V(1), V(2), and V(3) into n (n is an integer equal to or more than 2) regions based on A-scan signals AS1, AS2, and AS3 extracted from three measurement light beams constituting measurement light beams Bm. Assume that the tomograms V(1), V(2), and V(3) each are constituted by 128 B-scan images (Ly=128), and n is 4. In this case, therefore, the tomogram selection unit 140 obtains 12 region tomograms VR(a, b) where a is a number a (a={1, 2, 3}) of a three-dimensional tomogram, and b is the bth region of each three-dimensional tomogram (b={1, 2, 3, 4}).

In this case, considering the fact that when positional offset correction is independently performed for each region, a relative positional offset remains between the regions, the tomography apparatus according to this embodiment sets common B-scan images at the boundaries between adjacent regions so as to maintain the continuity of the regions of the three-dimensional tomogram. That is, the first to 33rd B-scan images constitute V(a, 1). The 33rd to 65th B-scan images constitute V(a, 2). The 65th to 97th B-scan images constitute V(a, 3). The 97th to 128th B-scan images constitute V(a, 4).

Like equation (8), an accumulated value P(w, b) of feature amounts is calculated for each region. This embodiment, however, accumulates values within the range of the bth region. The embodiment then obtains one of the respective bth regions which has a maximum accumulated value P by using equation (11) given below.

$$P(r, b) = \underset{w}{\operatorname{argmax}}(P(w, b)) \quad (11)$$
$$0 \le w < Lw$$

where V(r, b) indicates that the rth three-dimensional tomogram is selected as a standard region tomogram from the bth region (b is one of 1 to n). A number r of the standard region tomogram selected from the respective bth regions (b={1, 2, 3, 4}) is transferred to the storage unit 130 and the tomogram position correction unit 150.

In step S1050, the tomogram position correction unit 150 performs positional offset correction for the respective B-scan images constituting the standard region tomogram V(r, b) for each bth region selected in step S1040. The tomogram position correction unit 150 then performs positional offset correction for the corresponding regions of other three-dimensional tomograms by using the result of the above correction. Since positional offset correction performed for three-dimensional tomograms in this embodiment is basically the same as tomogram position correction processing shown in FIG. 11 in the second embodiment, a description of the processing will be omitted. Note however that this embodiment performs this processing for each region tomogram.

As is obvious from the above description, the tomography apparatus according to this embodiment is configured to segment each of a plurality of three-dimensional tomograms, obtained by concurrently performing imaging using a plurality of measurement light beams, into a plurality of regions. The apparatus then selects a standard region tomogram suitable for positional offset correction from each region. The apparatus is further configured to perform positional offset correction similar to that in the first embodiment for B-scan images constituting a standard region tomogram. On the other hand, the apparatus is configured to perform positional offset correction for B-scan images constituting regions of other three-dimensional tomograms which correspond to the standard region tomogram by using the positional offset correction result on the standard region tomogram, based on the relative positional relationship.

This makes it possible to accurately correct the positional offsets between a plurality of B-scan images of a three-dimensional tomogram.

Fourth Embodiment

The second embodiment described above is configured to search for a standard three-dimensional tomogram suitable for positional offset correction based on feature amounts. However, the present invention is not limited to this. For example, the present invention may be configured to separately apply measurement light (standard measurement light) capable of generating a standard three-dimensional tomogram suitable for positional offset correction and select the three-dimensional tomogram generated based on the standard measurement light as a standard three-dimensional tomogram. This embodiment will be described in detail below.

<1. Arrangement of Tomography Apparatus>

FIG. 12 is a block diagram showing the overall arrangement of a tomography apparatus 1200 according to the fourth embodiment of the present invention. As shown in FIG. 12, the tomography apparatus 1200 includes a tomogram acquisition unit 1210, a storage unit 130, a tomogram selection unit 140, a tomogram position correction unit 150, a tomogram output unit 160, and a measurement light setting unit 1270.

Note that in the tomography apparatus 1200, the tomogram acquisition unit 1210 is configured to irradiate a measurement target with a plurality of measurement light beams corresponding to irradiation conditions. Assume that the measurement light setting unit 1270 is configured to set various irradiation conditions (a measurement position, measurement sensitivity, resolution, and the like) of measurement light beams emerging from the tomogram acquisition unit 1210.

<2. Detailed Arrangement of Tomogram Acquisition Unit>

Figure 13:
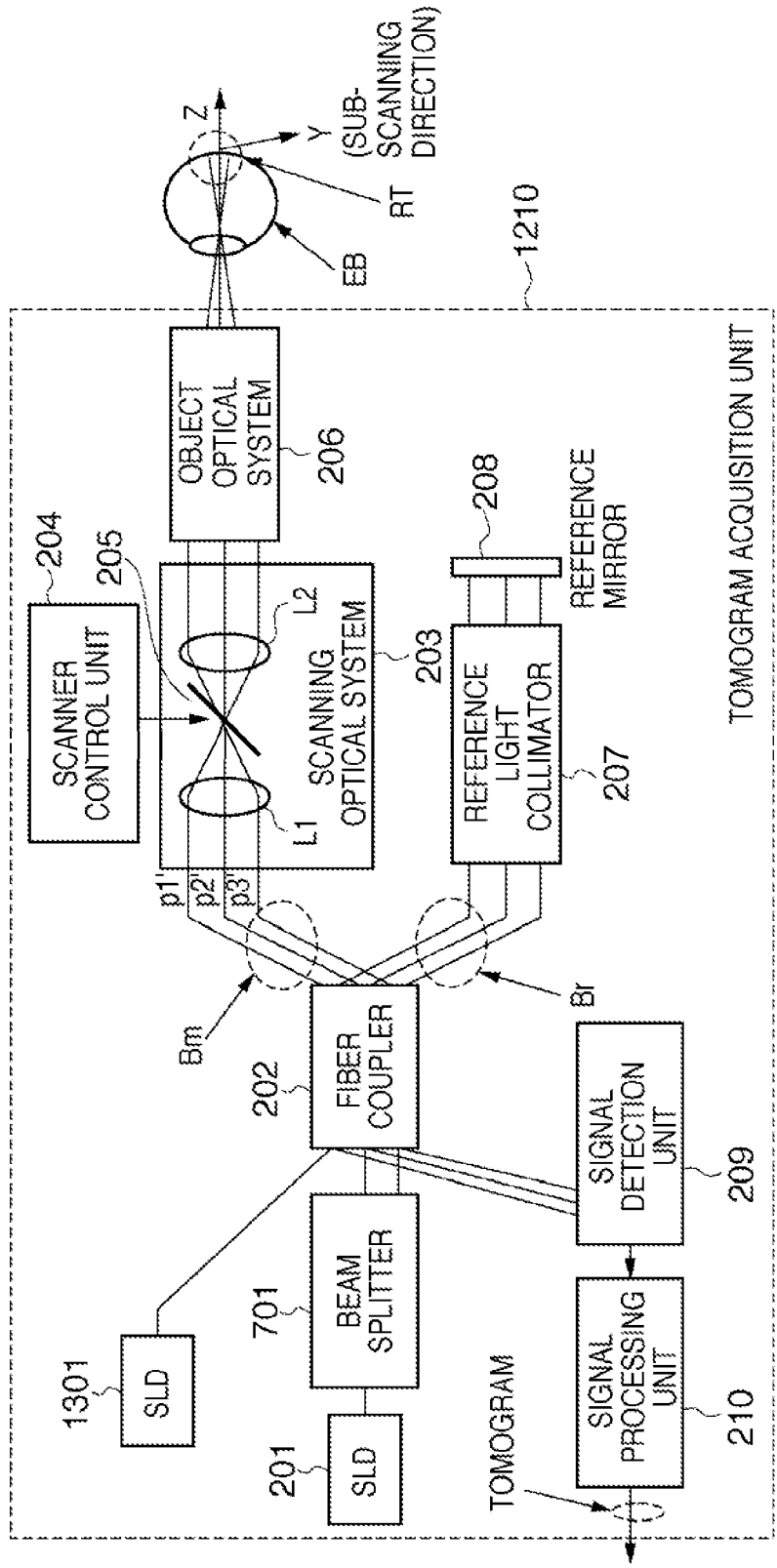
FIG. 13 is a block diagram showing the detailed arrangement of a tomogram acquisition unit.

FIG. 13 is a block diagram showing the detailed arrangement of the tomogram acquisition unit 1210 of the tomography apparatus 1200 according to this embodiment. Since the arrangement of the tomogram acquisition unit 1210 according to this embodiment is basically the same as that of the tomogram acquisition unit 700 described with reference to FIG. 7 in the second embodiment, different points between the embodiments will be mainly described below.

The tomogram acquisition unit 1210 differs from the tomogram acquisition unit 700 shown in FIG. 7 in that an SLD 1301 which emits light different from that emitted by the SLD 201 is added, and the light emitted by the SLD 201 is split into two light beams by a beam splitter 701.

With this arrangement, three light beams strike a fiber coupler 202. The three light beams include one light beam emitted from the SLD 1301 and two light beams obtained by splitting the light emitted by the SLD 201 through the beam splitter 701. In this embodiment, the light emitted by the SLD 201 (second irradiation means) is, for example, light having a wavelength of 840 nm. The light emitted by the SLD 1301 (first irradiation means) is, for example, light (standard measurement light) having a wavelength of 1050 nm.

The fiber coupler 202 which has received three light beams separates each light beam into a measurement light beam Bm and a reference light beam Br. Of these light beams, the measurement light beams Bm (p1', p2', and p3') strike a scanning optical system 203 through optical fibers.

The scanning optical system 203 includes a lens L1, and focuses the incident measurement light beams Bm on a galvanometer mirror 205. The galvanometer mirror 205 scans a fundus retina RT as a measurement target with the focused measurement light beams Bm.

Figure 14:
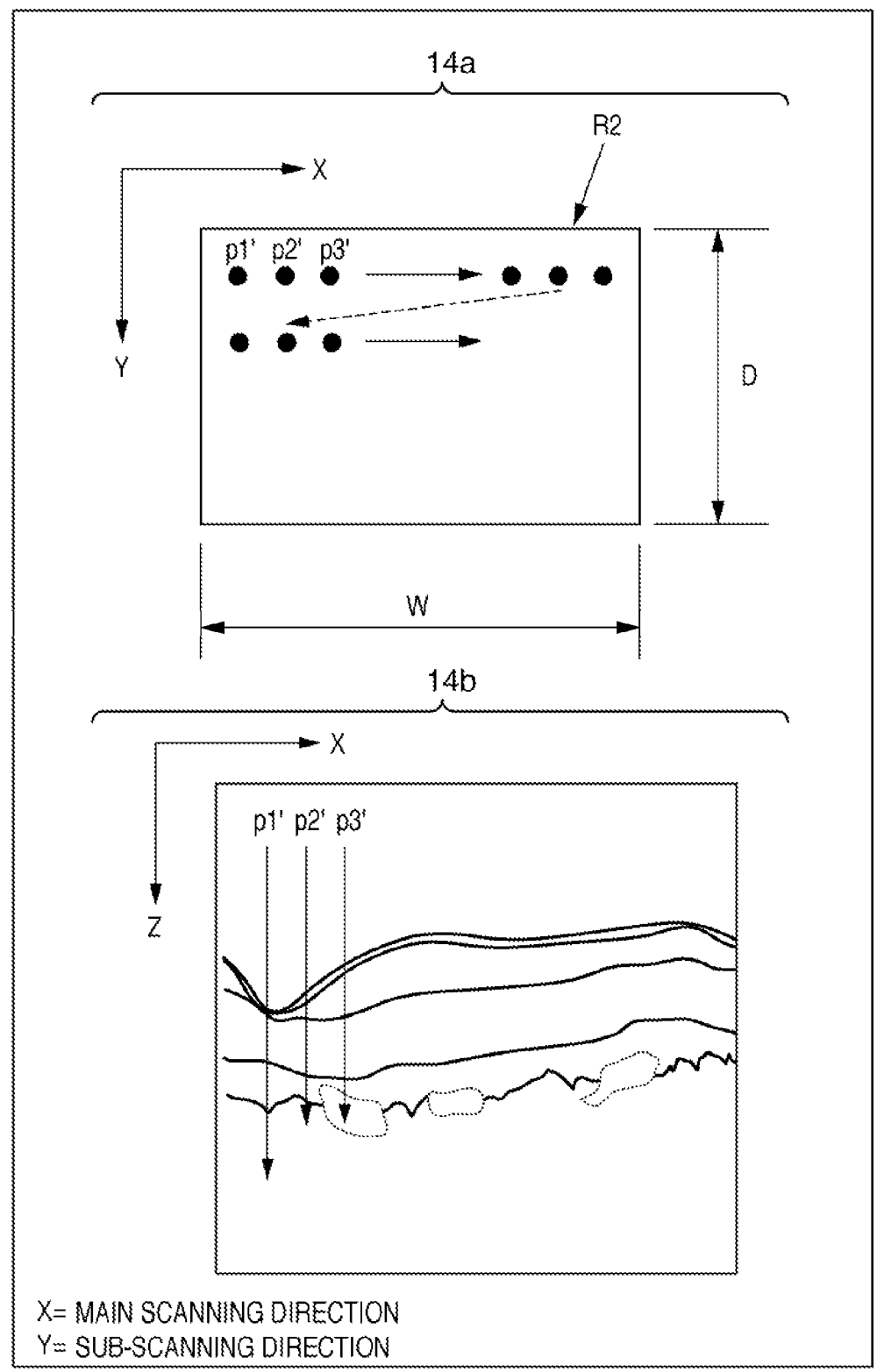
FIG. 14 is a view showing how a plurality of B-scan images are acquired.

FIG. 14 is a view showing how B-scan images are acquired by scanning the measurement light beams Bm output from the scanning optical system 203 on the fundus retina RT as a measurement target. As indicated by 14*a* of FIG. 14, the three measurement light beams Bm output from the scanning optical system 203 move parallel in the main scanning direction. 14*b* of FIG. 14 shows the relationship between the B-scan images generated in this case and the respective measurement light beams forming the measurement light beams Bm. As described above, the measurement light beam p1' of the measurement light beams Bm has a longer wavelength than the measurement light beam p2' and the measurement light beam p3'. Therefore, the measurement light beam p1' reaches a deeper region than the measurement light beams p2' and p3'.

In this case, a thick blood vessel called a choroid runs in a deep region in the fundus retina RT. For this reason, the B-scan image generated based on the measurement light beam p1' has higher contrast than the B-scan images generated based on the measurement light beams p2' and p3'.

In general, in examination of the fundus, it is desireble to image the retinal layer above the choroid at a high resolution. However, the retinal layer has a layered structure in geometric term, and hence exhibits little changes along the X-axis direction. This makes it difficult to obtain feature amounts for positional offset correction.

In contrast to this, since a measurement light beam (standard measurement light beam) having a long wavelength can image a B-scan image including the choroid, it is possible to generate a B-scan image having a feature in the X-axis direction. That is, it is possible to extract effective feature amounts for accurate positional offset correction between B-scan images.

<3. Explanation of Tomography/Correction Processing>

Figure 15:
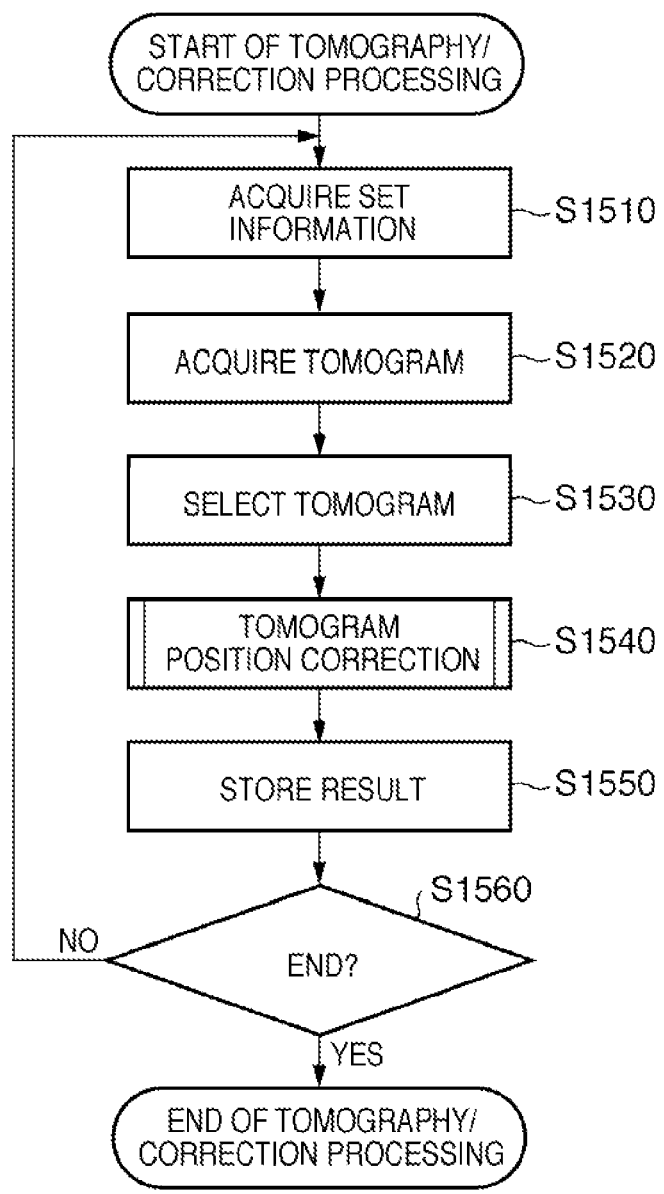
FIG. 15 is a flowchart showing a procedure for tomography/correction processing.

A procedure for tomography/correction processing in the tomography apparatus according to this embodiment will be described next. FIG. 15 is a flowchart showing a procedure for tomography/correction processing in the tomography apparatus according to the embodiment.

As shown in FIG. 15, when starting tomography/correction processing, the apparatus acquires various kinds of set information input by the operator via a keyboard, a mouse, and the like (not shown) in step S1510. The apparatus transmits the information to the tomogram acquisition unit 1210.

Note that since the set information has already been described in detail in the first and second embodiments, a description of the information will be omitted. Assume however that the tomography apparatus according to this embodiment acquires and transmits set information associated with irradiation conditions for the respective measurement light beams, in addition to the set information described in the second embodiment.

More specifically, the apparatus acquires and transmits irradiation conditions set such that one of three measurement light beams has a longer wavelength than the remaining two measurement light beams. In addition, the apparatus acquires and transmits irradiation conditions set such that the focus position of the measurement light beam set to have a longer wavelength is set, as the focus position of an object optical system 206, at a deep position in the depth direction (Z-axis direction).

In step S1520, the tomogram acquisition unit 1210 starts capturing a three-dimensional tomogram based on the transmitted set information. Note that the three-dimensional tomogram generated by the tomogram acquisition unit 1210 has already been described in the second embodiment, a description of the tomogram will be omitted. However, the tomography apparatus according to this embodiment averages the A-scan signals generated based on the measurement light beams p2' and p3' of the three measurement light beams. For this reason, one B-scan image is generated based on the measurement light beams p2' and 3'. On the other hand, one B-scan image is generated from the A-scan signal generated based on the measurement light beam p1'. The generated B-scan images are transmitted as three-dimensional tomograms to a storage unit 130.

Averaging the A-scan signals generated based on the two measurement light beams p2' and p3' in this manner can generate a B-scan image with a high S/N ratio.

In step S1530, the tomogram selection unit 140 selects the three-dimensional tomogram reconstructed based on the measurement light beam (standard measurement light beam) p1' as a standard three-dimensional tomogram, and transmits the selection result to a tomogram position correction unit 1250. This makes it possible to select, as a standard three-dimensional tomogram, a three-dimensional tomogram in which the contrast of the choroid is high, and which is suitable for positional offset correction.

In step S1540, the apparatus performs positional offset correction between the respective B-scan images constituting the standard three-dimensional tomogram. Subsequently, the apparatus performs positional offset correction for the three-dimensional tomogram generated based on the two measurement light beams p2' and p3' based on the relative positional relationship. Note that since such positional offset correction has already been described with reference to FIG. 11 in the second embodiment, a description of the correction will be omitted.

In addition, since the processing in steps S1550 and S1560 is the same as that in steps S1060 and S1070 in the second embodiment, a description of the processing will be omitted.

As is obvious from the above description, this embodiment is configured to separately apply a measurement light beam (standard measurement light beam) having a long wavelength which is capable of generating a three-dimensional tomogram suitable for positional offset correction (containing effective feature amounts for positional offset correction), in addition to a measurement light beam suitable for imaging a measurement target.

This makes it possible to generate a three-dimensional tomogram suitable for positional offset correction and perform positional offset correction for other three-dimensional tomograms by using the positional offset correction result on the three-dimensional tomogram based on the relative positional relationship.

Although the number of light beams constituting measurement light beams is three in this embodiment, the present invention is not limited to three. It is possible to form measurement light beams by using an arbitrary number of light beams including at least one measurement light beam (standard measurement light beam) having a long wavelength which is capable of generating a three-dimensional tomogram suitable for positional offset correction.

This embodiment is configured to select, as a standard three-dimensional tomogram, the three-dimensional tomogram generated based on a measurement light beam (standard measurement light beam) having a long wavelength which is capable of generating a three-dimensional tomogram suitable for positional offset correction. However, the present invention is not limited to this. For example, the present invention may be configured to properly select either the three-dimensional tomogram generated based on a measurement light beam suitable for imaging of a measurement target or the three-dimensional tomogram based on a measurement light beam (standard measurement light beam) having a long wavelength which is suitable for positional offset correction, which is more suitable for positional offset correction.

Figure 16:
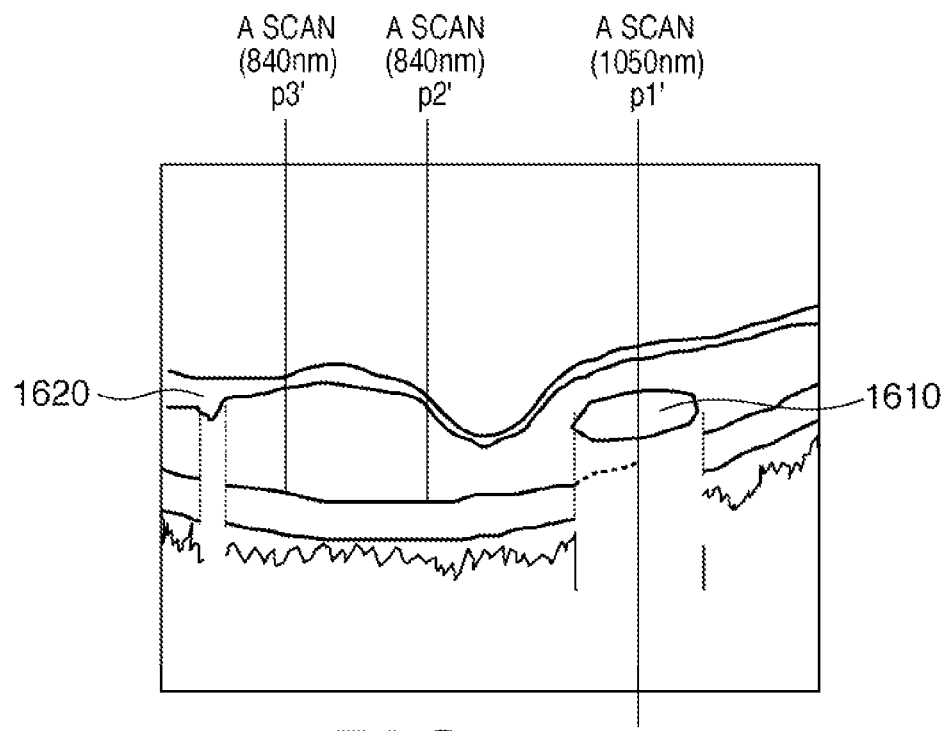
FIG. 16 is a view showing a B-scan image when the retinal layer has a leukoma.

This arrangement is especially effective for a case in which the retinal layer has a lesion such as a leukoma, and a standard measurement light beam cannot reach the choroid. FIG. 16 is a view showing a case in which the retinal layer has a leukoma, and a standard measurement light beam (wavelength=1050 nm) cannot reach the choroid. When a standard measurement light beam cannot capture a three-dimensional tomogram of the choroid, it is not possible to perform accurate positional offset correction even by using the three-dimensional tomogram generated based on the measurement light beam as a standard three-dimensional tomogram.

If the retinal layer has a lesion such as a leukoma, the three-dimensional tomogram generated based on a measurement light beam (wavelength=840 nm) suitable for imaging of a measurement target includes feature amounts effective for positional offset correction. In such a case, selecting, as a standard three-dimensional tomogram, the three-dimensional tomogram generated based on the measurement light beam suitable for imaging of the measurement target can improve the accuracy of positional offset correction.

In addition, this embodiment is configured such that even if measurement light beams include measurement light beams having different wavelengths, a common reference mirror is used as a reference mirror which reflects corresponding reference light beams. However, the present invention is not limited to this. For example, the present invention may be configured to separately include a reference mirror which reflects reference light having a long wavelength. This makes it possible to set the position of a coherence gate for a measurement light beam (standard measurement light beam) having a long wavelength at a deeper position than the position of a coherence gate for another measurement light beam. More specifically, it is possible to adjust the movable range of the reference mirror which reflects reference light having a long wavelength such that the coherence gate is located in a region closer to the choroid.

In this embodiment, even if measurement light beams include standard measurement light beams having different wavelengths, the focus positions of the respective measurement light beams focused by the object optical system 206 are common to each other. The present invention is not limited to this. For example, the embodiment may be configured to set the focus position of a standard measurement light beam having a long wavelength at a position far from the focus position of another measurement light beam.

Figure 17:
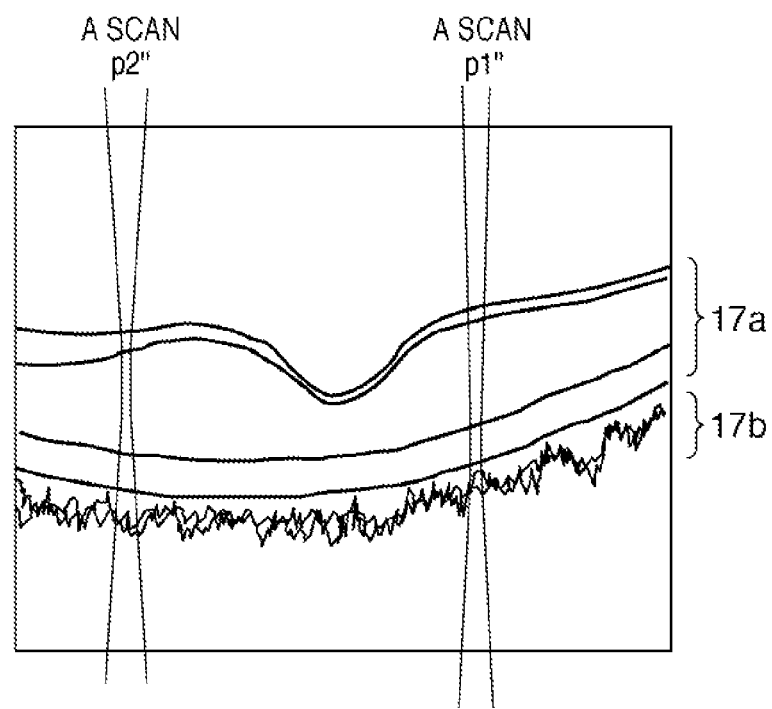
FIG. 17 is a view showing how the focus position is changed.

FIG. 17 is a view showing how the focus positions are changed between measurement light beams having different wavelengths. Referring to FIG. 17, 17a indicates the retinal layer, and 17b indicates the choroid. In the case of FIG. 17, the focus position of a measurement light beam p2" is set at the retinal layer, and the focus position of a measurement light beam p1" is set at the choroid.

At the focus position, a measurement light beam is focused most, and the contrast increases at the same time when the measurement resolution increases. As in the case of FIG. 17, setting the focus position of the measurement light beam p1" at the choroid can improve the resolution and contrast of a B-scan image of the choroid. As a consequence, it is possible to perform positional offset correction for tomograms with higher accuracy.

Fifth Embodiment

The second embodiment is configured to scan a plurality of measurement light beams on different regions to form different three-dimensional tomograms. However, the present invention is not limited to this. For example, the present invention is configured to arrange a plurality of measurement light beams which are scanned in conjunction with each other into the first and second arrays in the sub-scanning direction and cause the sub-scanning positions at which the measurement light beams arranged in the second array are applied previously to coincide with the sub-scanning positions at which the measurement light beams arranged in the first array are applied currently. The apparatus then acquires the B-scan images generated by the measurement light beams in the second array at the previous sub-scanning position and the B-scan images generated by the measurement light beams in the first array at the current sub-scanning position. This makes it possible to perform positional offset correction based on these B-scan images (the B-scan images generated based on the measurement light beams applied at the same position and different timings).

This embodiment will be described in detail below. Note that since the basic arrangement of the tomography apparatus according to this embodiment is the same as that of the second embodiment, a description of the arrangement will be omitted. Note however that since the detailed arrangement of a scanning optical system 203 of a tomogram acquisition unit 700 differs from that in the second embodiment, the scanning optical system 203 will be described below.

Figure 18:
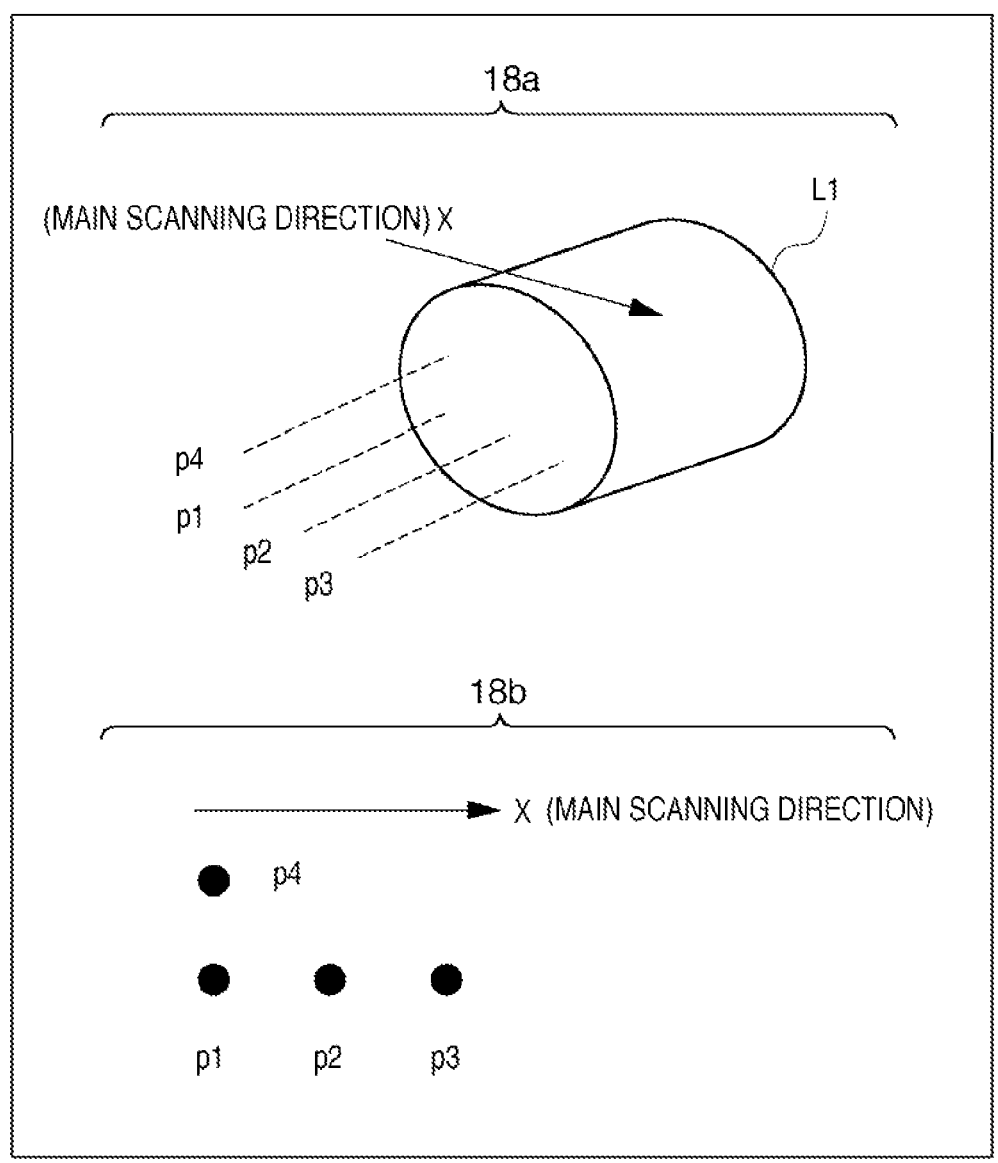
FIG. 18 is a view showing the arrangement of measurement light beams.

FIG. 18 is a view showing the arrangement of measurement light beams emerging from the scanning optical system 203 in the tomography apparatus according to this embodiment. As indicated by 18a of FIG. 18, in the tomography apparatus according to the embodiment, measurement light beams Bm are constituted by four measurement light beams. As indicated by 18b of FIG. 18, of the four measurement light beams, measurement light beams p1 to p3 (second measurement light beams) are arranged parallel in the main scanning direction, and a measurement light beam p4 (first measurement light beam) is shifted from the measurement light beams p1 to p3 in the sub-scanning direction.

Figure 19:
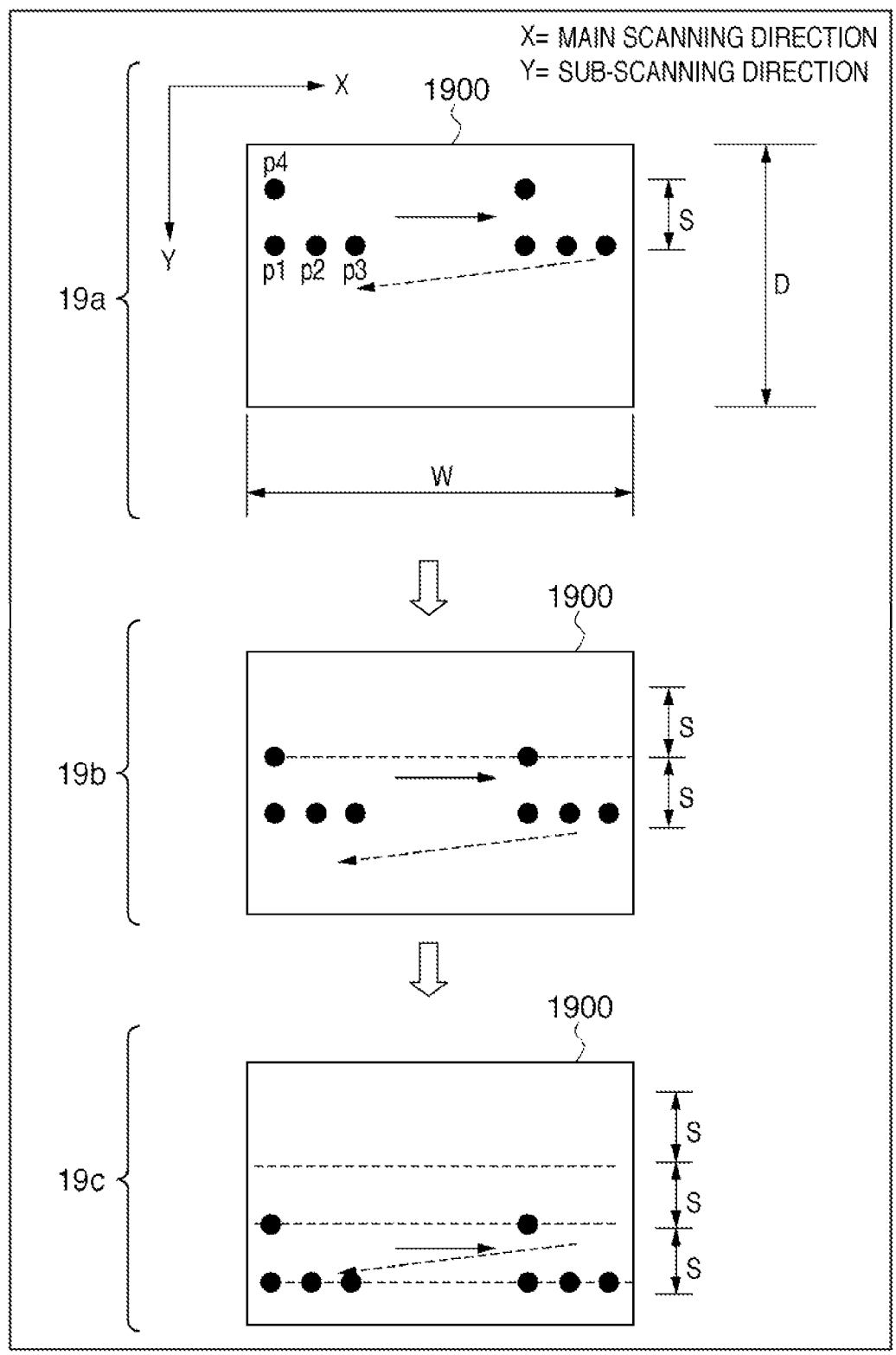
FIG. 19 is a view showing how a plurality of measurement light beams scan in the main scanning direction and the sub-scanning direction.

FIG. 19 is a view showing how the measurement light beams p1 to p4 in this arrangement are scanned in the main scanning direction and the sub-scanning direction. In 19a of FIG. 19, reference numeral 1900 denotes an imaging region on the fundus retina RT, and the measurement light beams p1 to p4 scan in the imaging region 1900. Reference symbol W denotes the number of A-scan signals in the X-axis direction (main scanning direction) in the imaging region 1900; D, the number of B-scan images in the Y-axis direction (sub-scanning direction); and s, the offset amount between the irradiation positions of the measurement light beams p1 to p3 and the irradiation position of the measurement light beam p4 (the offset amount in the sub-scanning direction).

As indicated by 19a of FIG. 19, scanning the measurement light beams p1 to p4 in the main scanning direction will generate W A-scan signals in the X-axis direction (main scanning direction) based on the respective measurement light beams.

Since the measurement light beams p1 to p3 are arranged horizontal, when the measurement light beams are scanned in the main scanning direction, the measurement light beams are scanned at the same position with predetermined time lags. For this reason, A-scan signals obtained when the measurement light beams are scanned at the same position are averaged to reduce noise. This makes it possible to generate a B-scan image with high image quality and a high S/N ratio based on measurement values p1 to p3 (second generating means). In this case, the B-scan image with high image quality generated in this manner will be referred to as HB(py). Note that py indicates the scanning position in the sub-scanning direction on the fundus retina.

On the other hand, since the measurement light beam p4 is shifted from the measurement light beams p1 to p3 in the sub-scanning direction, it is not possible to average the A-scan signals generated by the measurement light beam p1 and other measurement light beams. For this reason, the B-scan image generated based on the measurement light beam p4 is a B-scan image with low image quality (first generating means). Note that such a B-scan image will be referred to as LB(py).

19b of FIG. 19 shows how the measurement light beams p1 to p4 indicated by 19a of FIG. 19 move in the sub-scanning direction after scanning of them in the main scanning direction is complete.

As indicated by 19b of FIG. 19, the moving amount of the measurement light beams p1 to p4 in the sub-scanning direction is s. That is, the measurement light beam p4 in the current scanning operation in the main scanning direction scans the sub-scanning position at which the measurement light beams p1 to p3 have scanned in the previous scanning operation in the main scanning direction. As a consequence, LB(py+s) and HB(py) are B-scan images at the same position in the sub-scanning direction.

Setting the moving amount s in the sub-scanning direction in this manner can perform positional offset correction for the B-scan image HB(py+s) by using the B-scan image LB(py+s) and the B-scan image HB(py).

As is obvious from the above description, the tomography apparatus according to this embodiment is configured to arrange a plurality of measurement light beams in a plurality of arrays in the sub-scanning direction. In addition, the embodiment is configured to make the offset amount between the irradiation positions of measurement light beams in the sub-scanning direction almost equal to the moving amount in the sub-scanning direction.

This makes it possible to compare the B-scan image generated by the measurement light beams in the mth array (m is an integer equal to or more than 1) at the previous sub-scanning position with the B-scan image generated by the measurement light beam in the (m−1)th array at the current sub-scanning position. It is possible to perform positional offset correction for the B-scan image generated by the measurement light beams in the mth array at the current sub-scanning direction by using the position correction value calculated based on the comparison between the B-scan images.

This makes it possible to accurately correct the positional offsets between a plurality of B-scan images of a three-dimensional tomogram.

Sixth Embodiment

The fifth embodiment described above is configured to perform positional offset correction for B-scan images by using the position correction values calculated based on the B-scan image at the previous sub-scanning position and the B-scan image at the current sub-scanning position. However, the present invention is not limited to this. For example, the present invention may be configured to control the scanning speed and scanning position of a measurement light beam at the current sub-scanning position by using calculated position correction values. This embodiment will be described in detail below.

<1. Arrangement of Tomography Apparatus>

Figure 20:
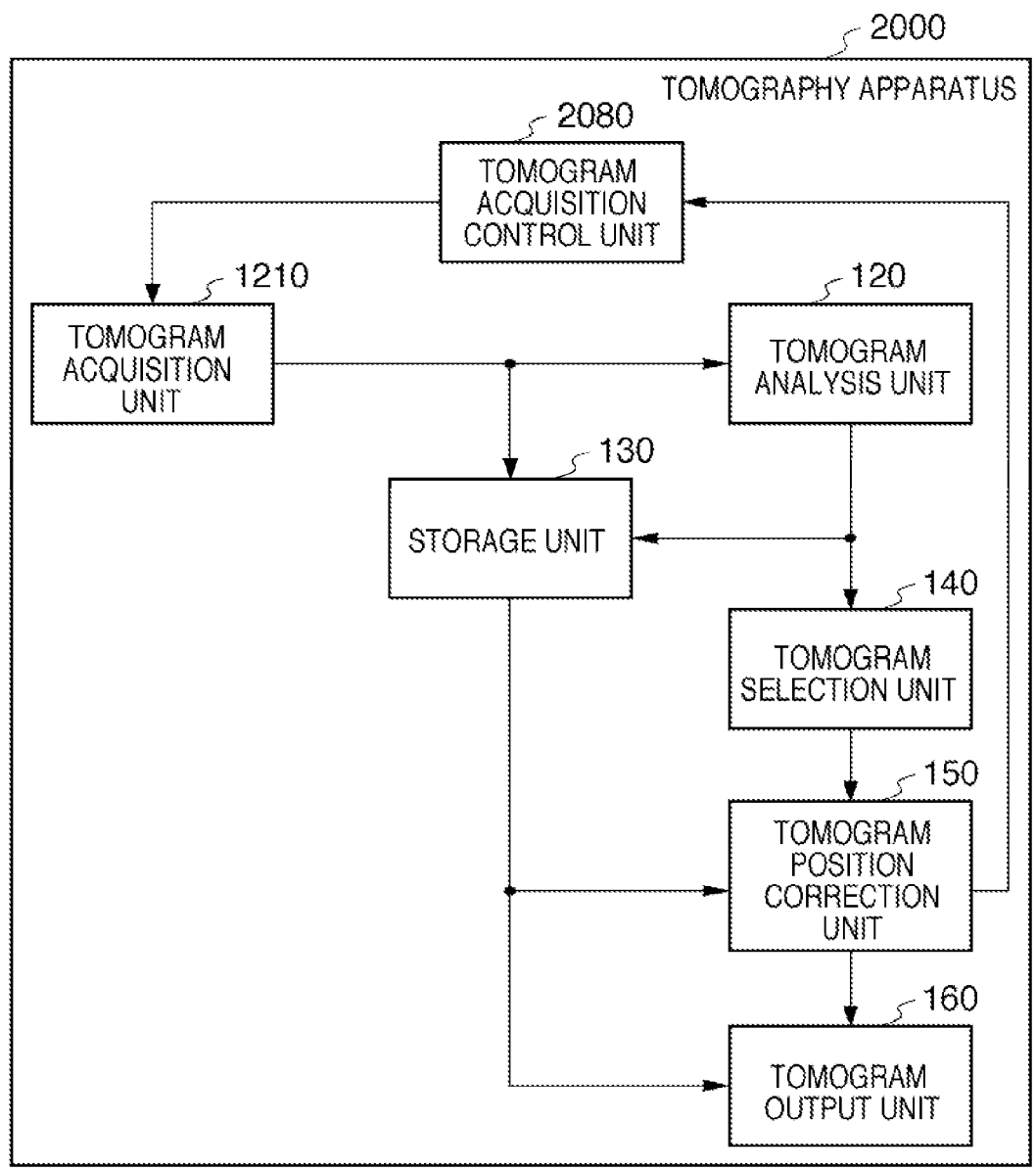
FIG. 20 is a block diagram showing the overall arrangement of a tomography apparatus.

FIG. 20 is a block diagram showing the overall arrangement of a tomography apparatus 2000 according to the sixth embodiment of the present invention. As shown in FIG. 20, the tomography apparatus 2000 includes a tomogram acquisition unit 1210, a tomogram analysis unit 120, a storage unit 130, a tomogram selection unit 140, a tomogram position correction unit 150, a tomogram output unit 160, and a tomogram acquisition control unit 2080.

Note that since the tomogram acquisition unit 1210 has been described in detail with reference to FIG. 13 in the fourth embodiment, a detailed description of the unit will be omitted. The tomogram acquisition control unit 2080 controls the scanning speed and scanning position of each measurement light beam output from the tomogram acquisition unit 1210 based on the position correction values calculated by the tomogram position correction unit 150.

<2. Explanation of Tomography/Scanning Control Processing>

Figure 21:
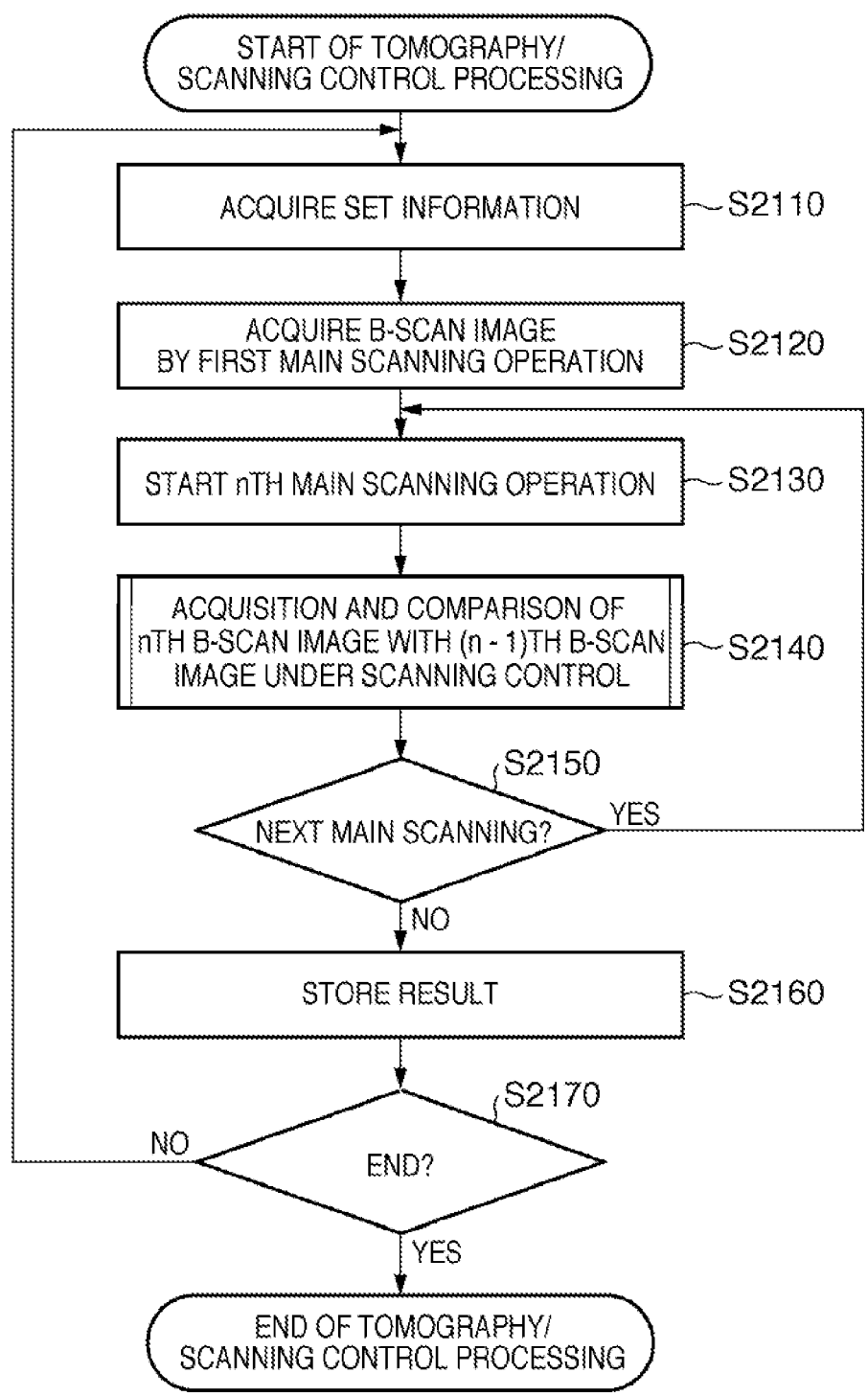
FIG. 21 is a flowchart showing a procedure for tomography/scanning control processing.

A procedure for tomography/scanning control processing in the tomography apparatus 2000 according to this embodiment will be described next. FIG. 21 is a flowchart showing a procedure for tomography/scanning control processing in the tomography apparatus 2000 according to this embodiment.

As shown in FIG. 21, when starting tomography/scanning control processing, the tomography apparatus acquires various kinds of set information input by the operator via a keyboard, a mouse, and the like (not shown) in step S2110. The apparatus transmits the information to the tomogram acquisition unit 1210. Note that since the set information has already been described in detail in the first and second embodiments, a description of the information will be omitted.

In step S2120, a tomogram acquisition unit 2010 starts capturing a three-dimensional tomogram based on the transmitted set information. The tomogram acquisition control unit 2080 outputs an instruction to the scanner control unit 204 to make the galvanometer mirror 205 scan a measurement light beam in the main scanning direction.

The tomogram acquisition control unit 2080 receives the B-scan images generated based on the measurement light beams from a signal processing unit 210. Note that the first scanning operation in the main scanning direction generates the B-scan images HB(py) and LB (py−s). Note that py indicates the scanning position on the fundus retina in the sub-scanning direction. In addition, s indicates the moving amount in the sub-scanning direction (=offset amount between irradiation positions of measurement light beams in first array and measurement light beam in second array).

In step S2130, the tomogram acquisition unit 2010 controls the galvanometer mirror 205 which scans a measurement light beam in the sub-scanning direction to change the nth (n is an integer equal to or more than 1) sub-scanning position of the measurement light beam. Scanning measurement light beams in the main scanning direction at the nth sub-scanning position will generate B-scan images HB(py+n×s) and LB(py+(n−1)×s).

In step S2140, the tomogram analysis unit 120 acquires a B-scan image LB(py+(n−1)×s) generated during scanning in the main scanning direction. The tomogram analysis unit 120 then compares this B-scan image with a B-scan image HB(py+(n−1)×s) generated when scanning is performed at the previous (n−1)th sub-scanning position in the main scanning direction. With this operation, the tomogram analysis unit 120 calculates a position correction value. In addition, the tomogram analysis unit 120 changes the scanning position and scanning speed in the current scanning operation in the main scanning direction based on the position correction values calculated by the tomogram position correction unit 150. Note that the tomography/scanning control processing in step S2140 will be described in detail below.

In step S2150, the apparatus determines whether scanning in the main scanning direction is to be performed at the (n+1)th sub-scanning position. If the apparatus determines in step S2150 that scanning in the main scanning direction is to be performed at the (n+1)th sub-scanning position, the process returns to step S2130 upon incrementing the value of n. If the apparatus determines in step S2150 that scanning in the main scanning direction is not to be performed at the (n+1)th sub-scanning position, the process advances to step S2160.

In step S2160, the storage unit 130 stores the three-dimensional tomogram generated based on the measurement light beams having undergone scanning control. In step S2170, the tomography apparatus 2000 determines whether it has received an instruction to end tomography/scanning control processing. Assume that the operator inputs an instruction to end tomography/scanning control processing via a keyboard or mouse (not shown). If the apparatus determines in step S2170 that it has received an instruction to end the tomography/scanning control processing, the apparatus terminates the tomography/scanning control processing. If the apparatus determines that it has accepted no instruction to end the tomography/scanning control processing, the process returns to step S2110 to execute tomography/scanning control processing for the fundus retina of the next object (or execute tomography/scanning control processing again for the fundus retina of the same object).

<3. Explanation of Tomography/Scanning Control Processing>

Figure 22:
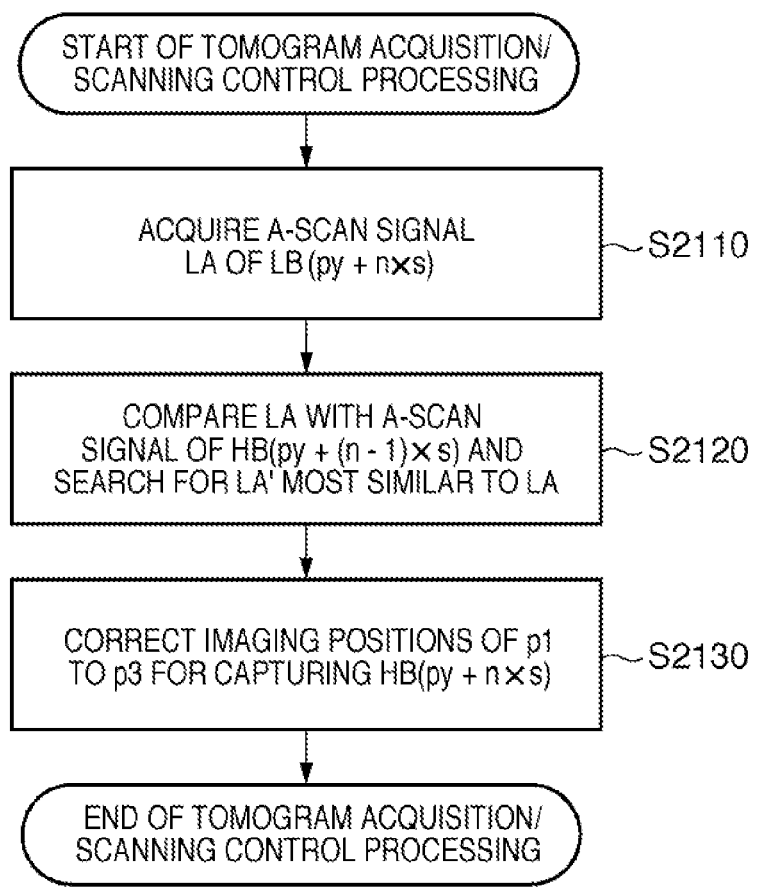
FIG. 22 is a flowchart showing a procedure for tomogram acquisition/scanning control processing.
Figure 23:
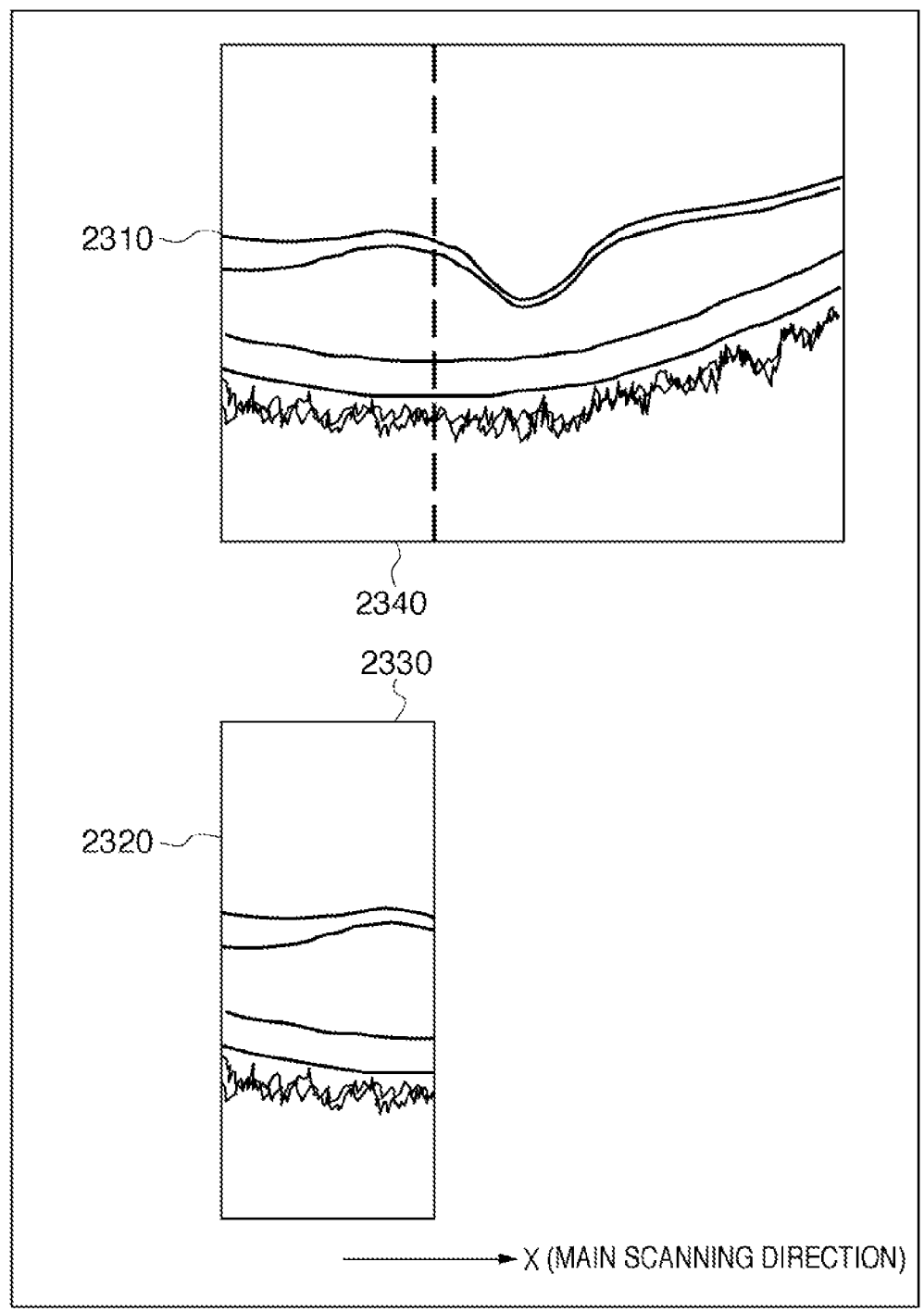
FIG. 23 is a view showing an example of a B-scan image HB and B-scan image LB.

A procedure for tomography/scanning control processing (step S2140) will be described next with reference to FIGS. 22 and 23. FIG. 22 is a flowchart showing a procedure for tomography/scanning control processing. FIG. 23 is a view showing the B-scan image HB(py+(n−1)×s) generated at the (n−1)th sub-scanning position and the B-scan image LB(py+(n−1)×s) which is being generated at the nth sub-scanning position.

In step S2210, the apparatus acquires an A-scan signal LA generated by a measurement light beam p4 and acquired from the signal processing unit 210, that is, the A-scan signal LA of the B-scan image LB(py+(n−1)×s). Referring to FIG. 23, reference numeral 2320 denotes a B-scan image LB(py+(n−1)×s); and 2330, a corresponding A-scan signal LA.

In step S2220, the tomogram position correction unit 150 compares the A-scan signal LA acquired in step S2210 with an A-scan signal 2340 in the B-scan image HB(py+(n−1)×s) generated at the (n−1)th sub-scanning position. The tomogram position correction unit 150 then searches the A-scan signal 2340 for an A-scan signal LA' most similar to the A-scan signal LA 2330.

Referring to FIG. 23, the A-scan signal 2330 is the A-scan signal LA' most similar to the A-scan signal LA 2330. In this case, based on the estimation that the measurement light beam p4 on the retina is identical to the A-scan signal LA', the tomogram position correction unit 150 calculates position correction values for the measurement light beam p4.

In step S2230, the tomogram position correction unit 150 transfers the position correction values calculated in step S2230 to the tomogram acquisition control unit 2080. The tomogram acquisition control unit 2080 controls a scanner control unit 204 based on the position correction values so as to reduce the positional offset of the measurement light beam p4. This controls the scanning speeds and scanning positions of the measurement light beams p1 to p4.

As is obvious from the above description, the tomography apparatus according to this embodiment is configured to arrange a plurality of measurement light beams in a plurality of arrays in the sub-scanning direction. The apparatus is also configured to make the offset amount between the irradiation positions of measurement light beams in the sub-scanning direction almost equal to the moving amount in the sub-scanning direction. The apparatus is further configured to calculate position correction values based on the B-scan image generated by measurement light in the mth array at the previous sub-scanning direction and the A-scan signal which is being generated by measurement light in the (m−1)th array at the current sub-scanning position. The apparatus then controls the scanning speed and scanning position of a measurement light beam which is currently scanned at the current sub-scanning position, based on the calculated position correction values.

As a result, it is possible to accurately correct the positional offsets between a plurality of tomograms in a three-dimensional tomogram during imaging.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-165053 filed on Jul. 13, 2009, which is hereby incorporated by reference herein in its entirety.

The invention claimed is:

1. A tomography apparatus comprising:
a tomogram acquisition unit configured to acquire a plurality of tomograms;
an obtaining unit configured to obtain contrasts of the plurality of tomograms;
a tomogram selection unit configured to select a standard tomogram based on the contrasts obtained by said obtaining unit; and
a tomogram position correction unit configured to perform position correction for the plurality of tomograms by using the selected standard tomogram.

2. The tomography apparatus according to claim 1, wherein the contrast of the standard tomogram is higher than those of the other tomograms.

3. The tomography apparatus according to claim 1, wherein said tomogram position correction unit performs an alignment successively from a tomogram near to the standard tomogram.

4. The tomography apparatus according to claim 1, wherein the contrast is a value obtained by summing up the pixel value differences between pixels of a plurality of pixels included in each tomogram.

5. The tomography apparatus according to claim 1, wherein the plurality of tomograms are respectively obtained by irradiating an object with a plurality of measurement light beams.

6. The tomography apparatus according to claim 5, wherein the plurality of tomograms are respectively obtained by simultaneously irradiating an object with a plurality of measurement light beams when capturing the tomograms.

7. A tomography method comprising:
a tomogram acquisition step of causing a tomogram acquisition unit to acquire a plurality of tomograms;
an obtaining step of causing an obtaining unit to obtain contrasts of the plurality of tomograms;
a tomogram selection step of causing a tomogram selection unit to select a standard tomogram based on the contrast obtained in said obtaining step; and
a tomogram position correction step of causing a tomogram position correction unit to perform position correction for the plurality of tomograms by using the selected standard tomogram.

8. A non-transitory computer-readable storage medium storing a computer program for causing a computer to execute the steps of the tomography method according to claim 7.

* * * * *